United States Patent [19]
McNelis

[11] Patent Number: 5,446,203
[45] Date of Patent: Aug. 29, 1995

[54] SYNTHESIS OF HALOENONES AND ARYL OR ALKYL SUBSTITUTED ENONES OR ALKENES

[75] Inventor: Edward McNelis, New Rochelle, N.Y.

[73] Assignee: New York University, New York, N.Y.

[21] Appl. No.: 98,006

[22] Filed: Jul. 29, 1993

Related U.S. Application Data

[63] Continuation-in-part of Ser. No. 934,216, Aug. 25, 1992, abandoned.

[51] Int. Cl.⁶ .................................................. C07C 45/51
[52] U.S. Cl. ................................. 568/322; 568/361; 568/363; 568/404; 570/200; 570/216; 570/237
[58] Field of Search .............. 568/323, 361, 363, 404, 568/322, 362; 570/200, 216, 237

[56] References Cited

U.S. PATENT DOCUMENTS

| | | | |
|---|---|---|---|
| 1,023,907 | 8/1963 | Harper | 514/514 |
| 2,914,563 | 11/1959 | Allen | 568/323 |
| 4,536,516 | 8/1985 | Harper et al. | 568/323 |

FOREIGN PATENT DOCUMENTS 1013907 9/1962 United Kingdom ................ 568/323

OTHER PUBLICATIONS

Geetha J. Angara et al., α-Haloenones From Secondary Alkynols, Tetrahedron Letters, vol. 32:2099–2100 (1991).

Etienne-Emile Baulieu, On the Mechanism of Action of RU486, Annals New York Academy of Sciences, pp. 545–560, (1991).

Louis Rebrovic et al., Alkynylaryliodonium Tosylates and Aryl [β-(tosyloxy)vinyl]iodnium Tosylates from Reactions of Terminal Alkynes with [Hydroxy(tosyloxy)iodo]benzene, J. Org. Chem. 49:4700–4702 (1984).

R. Bryan Miller et al., Stereospecific Synthesis of (Z)-Tomoxifen via Carabometalation of Alkynylsilanes, J. Org. Chem., 50:2121–2123 (1985).

Paul L. Coe et al., Crossed Coupling of Functionalized Ketons by Low Valen Titanium (The McMurry Reaction): A New Steroselective Synthesis of Tamoxifen, J. Chem. Soc. Perkin Trans 1:475–477 (1986).

Anil K. Agarwal et al., Estrogen Receptor-binding Affinity of Tamoxifen Analogs with Various Side Chains and their Biologic Profile in Immature Rat Uterus, Steroids, vol. 56:486–489 (1991).

*Primary Examiner*—James H. Reamer
*Attorney, Agent, or Firm*—Browdy and Neimark

[57] ABSTRACT

Alternative methods for synthesizing haloenones and haloakenes and their use as starting materials for synthesis of substituted or unsubstituted alkyl and aryl substituted enones and alkenes, including tamoxifen and tamoxifen analogs, using such haloenones and haloalkenes.

21 Claims, No Drawings

SYNTHESIS OF HALOENONES AND ARYL OR ALKYL SUBSTITUTED ENONES OR ALKENES

CROSS-REFERENCE TO RELATED APPLICATIONS

This application is a continuation-in-part application of U.S. Ser. No. 07/934,216, filed on Aug. 25, 1992, now abandoned.

FIELD OF THE INVENTION

This invention relates to the field of synthetic organic chemistry. More particularly, the present invention involves alternative methods for synthesizing haloenones and haloalkenes, as well as for synthesizing alkyl and aryl substituted enones or alkenes, including tamoxifen and tamoxifen analogs, using haloenones or haloalkenes as starting or intermediate materials.

BACKGROUND OF THE INVENTION

Present methods for synthesizing stereospecific aryl or alkyl substituted alkene or enone compounds, such as tamoxifen and tamoxifen analogs, suffer from problems such as relatively low overall yields, low specificity, lack of stereospecificity, and high cost of starting compounds.

GB patent 1,013,907 discloses the synthesis of alkene derivatives according to the formula $R^1 R^2N(CH_2)_nO-\phi-CR^3=CR^4 R^5$ ("$\phi$" hereinafter stands for phenyl), wherein $R^1$ and $R^2$ are $C_{1-6}$ alkyl radicals; or wherein the $-N-R^1-R^2$ group is a nitrogen-containing heterocyclic radical, where n is 2-6, $R^3$ and $R^4$ are aryl radicals, optionally substituted by one or more alkyl, alkoxy and/or dialkylamino-alkoxy radicals and/or one or more halogen atoms; and wherein $R^5$ stands for an alkyl, alkenyl or aralkenyl radical. A process for synthesizing a compound according to the above formula is also disclosed including (1) dehydration of an alkanol derivative of formula $R^1R^2N(CH_2)_nO-\phi-R$, wherein R is $CR^3(OH)CHR^4R^5$ or $CHR^3C(OH)R^4R^5$.

Rebrovic and Koser, *J. Org. Chem.* 49:4700–4702 (1984) disclose that various terminal alkynes are found to react with (hydroxy(tosyloxy) iodo)benzene (HTIB) in $CHCl_3$ to give either aryl ($\beta$-(tosyloxy)vinyl) iodonium tosylates, or alkynylaryliodonium tosylates or a mixture thereof; however the HTIB is not disclosed, taught or suggested to function as a catalytic agent Miller and Al-Hassan, *J. Org. Chem.* 50:2121–2123 (1985) disclose a method for the stereospecific synthesis of (Z)-tamoxifen via carbomethylation of phenyl (trimethylsilyl) acetylene with diethylaluminum chloridetitanocene dichloride. However, such a synthetic scheme does not provide a commercially suitable method for synthesizing stereospecific tamoxifen for pharmaceutical preparation.

Coe and Scriven, *J. Chem. Soc. Perkin Trans.* 1:475–477 (1986) discloses the synthesis of tamoxifen by low valent titanium-mediated crossed coupling of substituted benzophenones according to the formula $R\phi CO\phi$, where $\phi$ is phenyl, R=MeO, $ClCH_2CH_2O$, $BrCH_2CH_2O$, $CF_3C_6H_4O$ and $Me_2NCH_2CH_2O$, where the stereospecificity with propriophenone provides the corresponding but-1-enes, such as tamoxifen with 88% yield, but with a Z:E rating of 3:1, thus having only a 67% specificity for the desired Z stereoisomer.

Accordingly, there remains a need to overcome the above problems by providing a method for synthesizing stereospecific substituted enone and alkene compounds, such as tamoxifen or tamoxifen analogs, and particularly the Z form of tamoxifen and analogs thereof, in commercially suitable amounts, with a high degree of stereospecificity, e.g., greater than 70% or 80%, and in relatively high yield.

SUMMARY OF THE INVENTION

It is an object of the present invention to overcome one or more deficiencies of the related art.

It is also an object of the present invention to provide new synthetic methods utilizing (hydroxy(tosyloxy) iodo)benzene (HTIB) or p-toluene sulfonic acid as catalysts for synthesizing haloenones which can be used as starting or intermediate materials for the synthesis of substituted or unsubstituted aryl and alkyl substituted enones and alkenes, such as tamoxifen or analogs thereof.

It is another object of the present invention to provide methods using stereospecific halogenation of substituted alkynols to provide haloenones.

It is still another object of the present invention to provide methods for the stereospecific synthesis of substituted or unsubstituted aryl and alkyl substituted aromatic arene compounds, as well as steroid derivatives and analogs thereof, utilizing HTIB or p-toluene sulfonic acid as catalysts for the synthesis of substituted or unsubstituted aryl or alkyl substituted haloenones or haloalkenes.

A further object of the present invention is to provide novel compounds using synthetic methods of the present invention, which compounds are useful for research, diagnostic, and therapeutic applications in animals, including mammals, birds and humans, such as the use of tamoxifen, or analogs thereof, or analogs thereof, as a chemotherapeutic agent, e.g., for treating breast cancer and estrogen receptor positive tumors.

According to one aspect of the present invention, a method is provided for synthesizing a substituted or unsubstituted aryl or alkyl-substituted haloenone, comprising (A) treating a tertiary or secondary alkynol with either (i) N-halosuccinimide and a catalytically effective amount off a (hydroxy(tosyloxy) iodo)benzene or p-toluene sulfonic acid; or (ii) $X_2O_5$ and $X_2$ in the presence of (hydroxy(tosyloxy)iodo) benzene or p-toluenesulfonic acid, where X is a halogen; under conditions to produce said haloenone in recoverable amounts; and (B) recovering said haloenone According to another aspect of the present invention, a method for synthesizing a haloalkene is provided, comprising (A) treating an alkyne with one selected from the group consisting of (i) N-halosuccinimide and a catalytically effective amount of a (hydroxy(tosyloxy) iodo)benzene or p-toluene sufonic acid; and (ii) $X_2/X_2O_5$ and $X_2$, in the presence of (hydroxy (tosyloxy) iodo) benzene or p-toluenesulfonic acid, where X is halogen; under conditions to produce said haloalkene in recoverable amounts; and (B) recovering said haloalkene.

In preferred embodiments, the above methods provide a haloenone or haloalkene having a stereospecificity of at least 70%, such as 75%, 77, 80, 82, 84, 86, 87, 89, 90, 92, 94, 95, 96, 98 or 99% stereospecificity.

According to another aspect of the present invention, a method for synthesizing a substituted or unsubstituted alkyl or aryl substituted enone or alkene is provided, comprising (A) carrying out a Stille or Heck synthesis using a haloenone or haloalkene as a starting or intermediate compound, such that the substituted enone or alkene is provided in recoverable amounts; and (B) recovering the substituted enone or alkene having a stereospecificity of at least 70%, such as 75%, 77, 79, 80, 82, 84, 86, 88, 89, 90, 92, 94, 95, 96, 98 or 99% stereospecificity.

In preferred embodiments, the above methods provide the haloenone or haloalkene as one selected from $\alpha$-,$\beta$-dihalo-; $\beta$-,$\beta$-dihalo-; and $\alpha$-,$\beta$-,$\beta$-trihalo-.

DETAILED DESCRIPTION OF THE PREFERRED EMBODIMENTS

New stereospecific synthetic methods, utilizing (hydroxy(tosyloxy)iodo)benzene (HTIB) or p-toluene-sulfonic acid as a catalytic reagent, have now been devised for the preparation of substituted or unsubstituted aryl or alkyl substituted enones and alkenes. Such methods provide superior intermediates and yields for the synthesis of substituted enones or alkenes from alkynols or alkynes. Such intermediates can include substituted or unsubstituted haloalkenes or haloenones which undergo substituted or unsubstituted aryl or alkyl halogen substitutions.

According to the present invention, the conversion of haloalkynols via a group shift to haloenones, by the use of HTIB (or p-toluene sulfonic acid) has been discovered to provide an unexpectedly high degree of botch selectivity and stereospecificity. Accordingly, methods of the present invention can be used to stereospecifically prepare and can selectively substitute with desired substituted or unsubstituted aryl or alkl groups, or substituted or unsubstituted haloenones or haloalkenes at the halo positions using known synthetic steps, as described herein.

Accordingly, the present invention provides methods for the production of substituted or unsubstituted aryl or alkyl substituted or unsubstituted enone or alkene compounds, which compounds are useful for diagnostic, therapeutic and research applications in mammals and birds, as well as for basic and clinical research, e.g., such as the non-limiting examples of tamoxifen and tamoxifen analogs (useful for treating estrogen positive tumors and breast cancers); steroid derivatives; and derivatives of Clomiphene.

According to another aspect of the present invention, haloalkynols can be converted to haloenones, which provide potential templates for selective and stereospecific exchanges of the halogen substituents for substituted or unsubstituted aryl or alkyl groups by catalysis involving known Stille or Heck reaction steps.

The present invention can include the synthesis of haloenones and haloalkenes having $\alpha$-,$\beta$-dihalo; $\beta$-$\beta$-dihalo-; and $\alpha$-,$\beta$-,$\beta$-trihalo substituents and their use as starting or intermediate materials for synthesis of substituted and unsubstituted alkyl and aryl substituted enones and alkenes, as described herein, such that the present invention is not limited to the specific examples presented herein, but includes any synthesis or use of haloenones as described herein.

Methods according to the following schemes (1), (2) or (3) of the present invention, as presented herein, may be used for producing substituted or unsubstituted aryl or alkyl substituted haloenones or haloalkenes, from which substituted or unsubstituted alkyl or aryl substituted alkenes can be produced. In schemes (1) and (2), halogenated alkynols may be stereospecifically prepared in high yield from alkynols, or, in scheme (3), halogenated alkenes may be prepared from alkynes, using at least one of (i) N-halosuccinimide (NXS) (such as N-bromosuccinimide (NBS) or N-iodosuccinimide (NIS)) in the presence of catalytic amounts of silver salts in acetone; (ii) NXS and catalytic amounts of (hydroxy(tosyloxy) iodo) benzene (hereinafter "HTIB" or "Koser's reagent"); or (iii) iodine and stoichiometric amounts of HTIB, wherein, in (ii) and (iii), HTIB can be replaced by p- toluene-sulfonic acid.

Additionally, as will be clear to one skilled in the art, corresponding alternative reagents involving NBS and bromine can be used for selective brominations, which are alternatively substituted for NIS and HTIB for selective iodinations, for producing halogenations of different halogens at different positions, e.g., at least one of $R^1$, $R^2$, $R^3$, $R^4$, and $R^5$ of formulae I–IV, as presented herein, such that selective and stereospecific substituted or unsubstituted alkyl or aryl substitutions may be made according to schemes (1), (2) or (3), to provide substituted enones or alkenes such as those of formulae (IB) and (IIB); or formulae (IC), (IIC), (IIIB) and (IV), respectively.

The solvent for the production of a haloenone or haloalkene may have an effect on the yield of the haloenones used in methods of the present invention. Known polar solvents have been found to provide recoverable yields of product according to the present invention, e.g., methanol, methyl acetate or ethyl acetate, with methanol preferred. Other suitable solvents include acetonitrile, but are not limited thereto.

In another non-limiting embodiment of the present invention, haloalkynols can be converted using halogens and oxides of halogens, such as iodine and oxides of iodine including as $I_2O_5$ (which is also effective for the conversion of tertiary alkynols to $\beta$-iodoenones). The tertiary alkynols can thereby be iodinated, such that haloenones, (e.g., $\beta$-,$\beta$-diiodoenones), are formed in high yields.

Once the haloenones are stereospecifically produced according to methods of the present invention, these compounds can be used as starting materials for the stereospecific replacement of the halogens with alkyl or aryl groups. This stereospecific replacement may be accomplished by the use of Stille or Heck reactions, which are well known (Stille, *Angew. Chem. Int. Ed. Engl.* 25:508 (1986) and Heck, *Palladium Reagents in Organic Synthesis*, Chapter 6, pp. 179–321 and Chapter 8, pp. 341–400, Academic Press London (1985), the contents of which references are entirely incorporated herein by reference). Examples of Stille reagents, include, e.g., $Me_3Ar_1Sn/Pd$, as well as other Stille or Heck reagents, zinc and/or tin in the presence of a palladium catalyst. Additionally, other known solvents can be used for such reactions, wherein methanol is preferred, according to known method steps.

The use of Stille or Heck reaction schemes for the production of enones and alkenes can be used to provide substituted or unsubstituted alkyl; aryl; alkyl-,aryl; alkyl-,diaryl; dialkyl-,aryl; dialkyl; diaryl; trialkyl; or triaryl enones and alkenes, based on the teaching and guidance presented herein, in combination with known method steps. The nature of the alkyl and aryl groups or the substituents thereon is not a significant portion of the present invention. As long as the selected moiety or substituent does not interfere with the basic reactions of the present invention they may be used and are considered as part of the present invention. Whether any given moiety or substituent interferes with the reaction can be determined without undue experimentation. Without limitation, preferred examples of operable groups include alkyl having 1-30 carbon atoms, including cycloalkyl optionally substituted with an alcohol, aldehyde, acid, amine, ester, ether, amide, halide, aryl, alkane, alkene or alkyne. The aryl groups may be substituted or unsubstituted cyclic or heterocyclic $C_5$-$C_{30}$ arenes such as benzyl, phenyl, toluyl, naphthyl, isophthalyl, anthracyl, phenanthracenyl, pyrenyl, cholesteryl derivatives, or steroids. The aryl groups may be substituted with any of the substituents discussed above for alkyl groups. The heterocyclic aryl groups may include pyridines, pyrrole, furane, thiophene, purine, or pyrimidine.

It has also been determined that the use of substituted or unsubstituted aryl or alkyl substituted or unsubstituted haloenones or haloalkenes, such as α-halo-; β-halo-; α-, β-dihalo-; α-, α-dihalo-; or β-, β-dihaloenones or alkenes, (e.g., diiodo, or dibromenones) as non-limiting examples, provide for stereospecific substitution by different substituted or unsubstituted aryl or alkyl groups, according to the present invention.

According to the present invention, a substituted or unsubstituted aryl or alkyl substituted alkynol can be treated with a $X_2/X_2O_5$, such as $I_2/I_2O_5$, to provide, e.g., an α-,β-dihalo-, α-,β-,β-trihalo- or α-α-dihaloenones or alkenes, which can then be used to stereospecifically substitute alky or aryl groups for the halo groups, as presented herein.

More particularly, substituted or unsubstituted haloenones or haloalkenes can be stereospecifically synthesized from tertiary or secondary alkynols, such as presented in scheme 1 or 2 below, as (IA) or (IIA), or, in another embodiment, by a tertiary alkyne (scheme 3) conversion to the α-halo alkyne or alkynol, using alternative reagents NXS/HTIB, $X_2/X_2O_5$, $X_2$/HTIB or NXS/$T_{SOH}$, or where HTIB is replaced by p-toluene sulfonic acid, such as NIS/HTIB; NBS/HTIB; $Br_2$/HTIB or $I_2$/HTIB, wherein HTIB can be replaced by p-toluene-sulfonic acid, as non-limiting examples.

According to another aspect of the present invention, a method according to scheme (1) is provided for synthesizing substituted or unsubstituted haloenones as intermediates or starting materials for substituted or unsubstituted aryl- or alkyl- substituted enones or alkenes such as those of at least step (1C), (1D) or (1E) of the following reaction scheme (1) using tertiary alkynols:

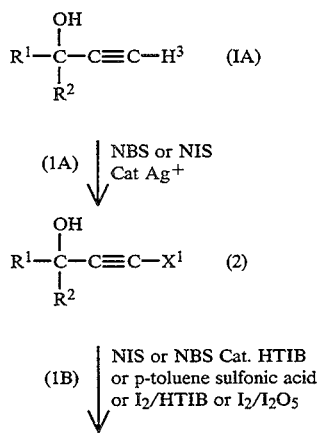

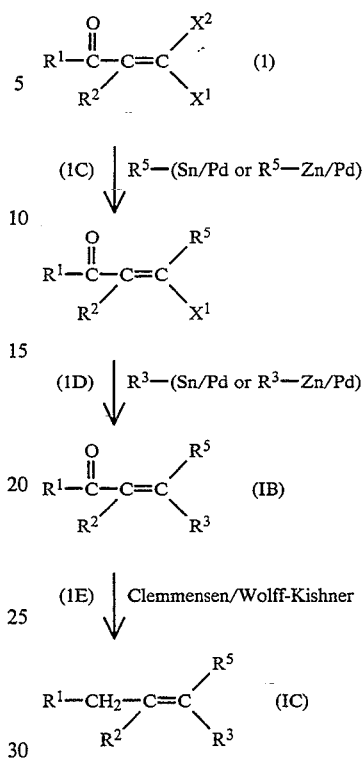

wherein $R^1$ is H or optionally substituted H, alkyl or aryl; $R^2$ is aryl or substituted aryl; $X^1$ and $X^2$ are each either I or Br; and $R^3$ and $R^5$ are as described below, for (IA), (IB) and (IC).

According to another aspect of the present invention, a method is provided for synthesizing cyclic haloenones as intermediates or starting materials for substituted enones or substituted alkenes according to at least step (2C) or (2D) of the following reaction scheme (2) using tertiary alkynols:

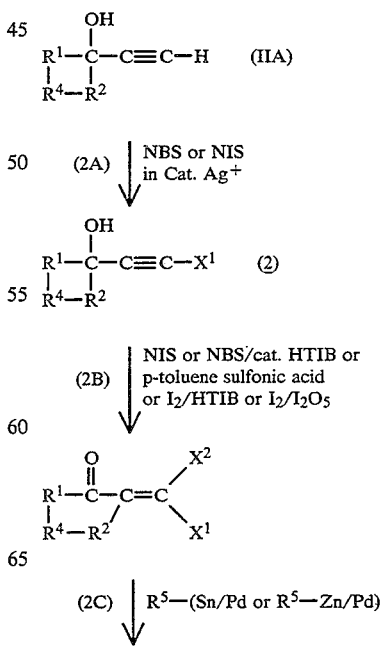

-continued

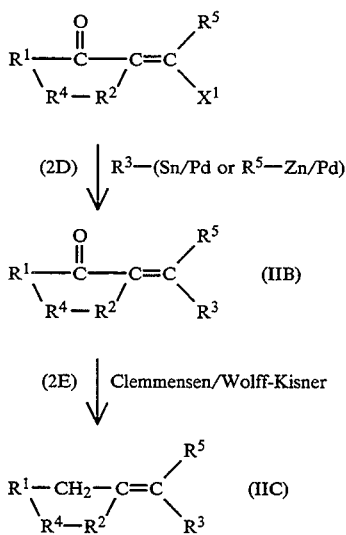

(2D) | $R^3$—(Sn/Pd or $R^5$—Zn/Pd)

(IIB)

(2E) | Clemmensen/Wolff-Kisner (IIC)

wherein. $R^1$, $R^2$, $X^1$ and $X^2$ are as described above. $R^3$, $R^4$ and $R^5$ are as described below.

According to another aspect of the present invention, a method is provided synthesizing haloalkynes as intermediate or starting materials for substituted alkenes according to at least one of (3B), (3C) or (3D) of the following reaction scheme (3) using tertiary alkynes:

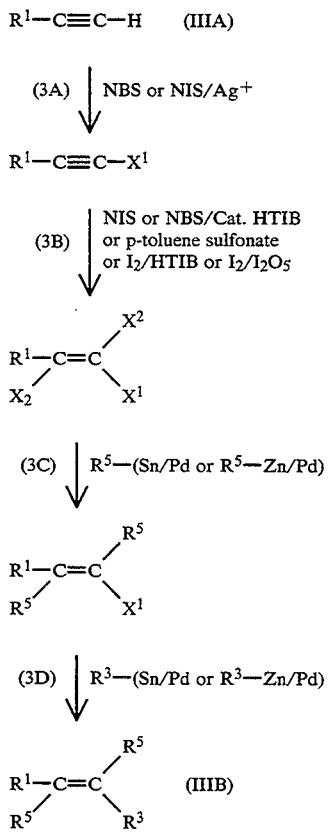

$R^1$—C≡C—H    (IIIA)

(3A) | NBS or NIS/Ag+

$R^1$—C≡C—$X^1$ (3B) | NIS or NBS/Cat. HTIB or p-toluene sulfonate or $I_2$/HTIB or $I_2/I_2O_5$ (3C) | $R^5$—(Sn/Pd or $R^5$—Zn/Pd)

(3D) | $R^3$—(Sn/Pd or $R^3$—Zn/Pd)

(IIIB)

wherein $R^1$, $X^1$ and $X^2$ are as described above; and $R^3$, $R^4$ and $R^5$ are as described below. $X^1$ and $X^2$ are preferably Br or I.

As a non-limiting example of a synthesis according to scheme (3), tamoxifen or tamoxifen analogs according to formula (IIIB) can be synthesized as follows:

$R^1$—C≡C—H    (IIIA)-1

(3A) | NBS catalytic Ag+

$R^1$—C≡C—Br (3B) | $I_2$/catalytic HTIB or $I_2/I_2O_5$ or $I_2$/HTIB

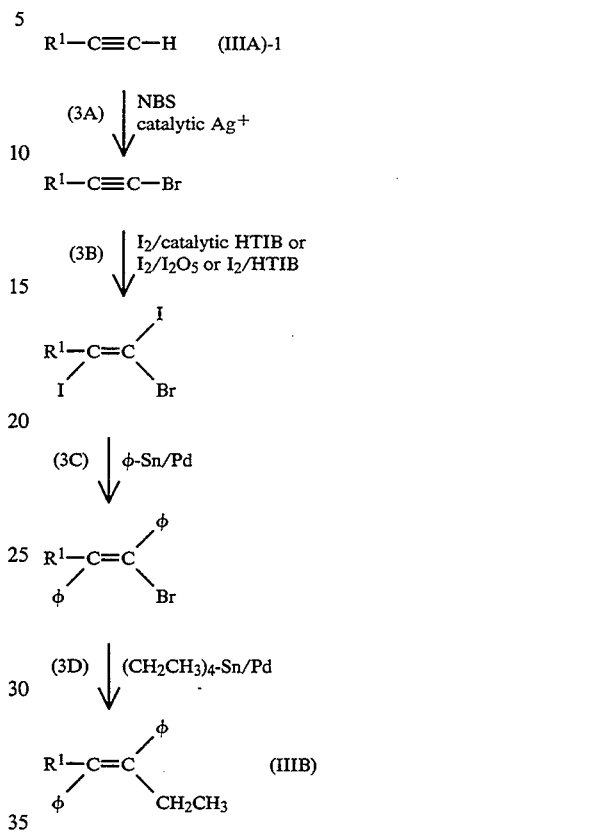

(3C) | φ-Sn/Pd (3D) | $(CH_2CH_3)_4$-Sn/Pd (IIIB)

wherein, $R^1$ is selected from φ-O—$CH_2CH_2N(CH_3)_2$, φ-O—$CH_2CH_2(N^+(CH_3)_2)CH_2CH_2N(CH_3)_2Cl$, φ-O—$CH_2CH(OH)CH_2N(NC_4H_4N)$φ$2HCl$ or φ-O—$CH_2CH_2Cl$ or an analog thereof.

According to another aspect of the present invention, starting or intermediate compounds which can be used in a method according to the present invention according to formula (IA):

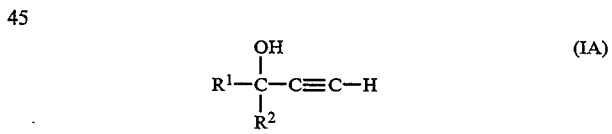

wherein $R^1$ is hydrogen, alkyl or aryl; $R^2$ is aryl or substituted aryl with substituents selected from alkyl, aryl, halo or alkoxyl.

According to another aspect of the present invention, intermediate or product compounds which can be used in a method according to the present invention are according to formula (IB):

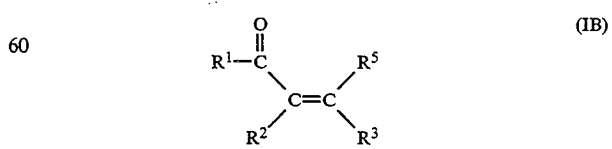

wherein $R^1$, $R^2$ and $R^3$ are as in (IA) above, and $R^5$ is hydrogen, alkyl, halo, aryl or substituted alkyl or aryl.

According to another aspect of the present invention, intermediate or product compounds which can be used in a method according to the present invention are according to formula (IC):

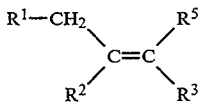

wherein $R^1$, $R^2$ and $R^3$ are as in (IA) above, and $R^5$ is hydrogen, alkyl, halo, aryl or substituted alkyl or aryl.

According to still another aspect of the present invention, starting or intermediate compounds which can be used in a method according to the present invention are those according to formula (IIA):

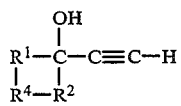

wherein $R^1$ and $R^2$ are each $CH_2$ or CH; $R^4$ is alkyl, O, cycloalkyl, cycloaryl, heterocycloalkyl or heterocycloaryl, such that $R^4$, $R^1$, $R^2$ and the hydroxy carbon form one to four cyclo or heterocyclo ring structures of 4, 5 or 6 members, preferably selected from O, C and N. When a single cyclo ring structure is formed, then $R^4$ is preferably $(CH_2)_n$, wherein n is 1, 2 or 3. The cycloalkyl or cycloaryl ring structures include steroids and analogs thereof.

According to a further aspect of the present invention, intermediate compounds which can be used in a method according to the present invention are those according to formula (IIB):

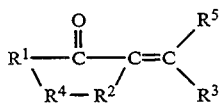

wherein $R^1$, $R^2$, and $R^4$ are as in (IIA) above, $R^3$ is hydrogen or halo, and $R^5$ is hydrogen or halo. The cycloalkyl or cycloaryl ring structures include steroids and analogs thereof.

According to still a further aspect of the present invention, intermediate compounds which can be used in a method according to the present invention are those according to formula (IIC):

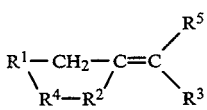

wherein $R^1$, $R^2$, and $R^4$ are as in (IIA) above, $R^3$ is as in (IA) above, and $R^5$ is as in (IB) above. The cycloalkyl or cycloaryl ring structures include steroids and analogs thereof.

According to another aspect of the present invention, intermediate and product compounds which can be used in a method according to the present invention are those the haloalkene is a compound according to formula IID:

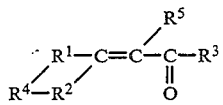

wherein $R^1$ and $R^2$ are each $CH_2$ or CH; $R^4$ is cycloalkyl, cycloaryl, heterocycloalkyl, or heterocycloaryl, such that $R^4$, $R^1$, $R^2$ and the alkene carbon from one to four cyclo or heterocyclic ring structures of 4, 5 or 6 members; $R^3$ is alkyl, aryl or substituted aryl with substituents selected from alkyl, aryl, halo or alkoxyl and $R^5$ is halo.

According to another aspect of the present invention, starting, intermediate and product compounds which can be used in a method according to the present invention are those according to formulae (IIIA) and (IIIB):

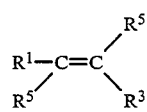

wherein $R^1$ is alkyl or aryl; $R^5$ is aryl or substituted aryl with substituents selected from alkyl, aryl, halo or alkoxyl.

In a preferred embodiment, a compound of formula (IIIB) may be a tamoxifen or a tamoxifen analog, such that $R^5$ is $\phi$; $R^3$ is $CH_2CH_3$; and $R^1$ may be selected from $\phi\text{-O}—CH_2CH_2N(CH_3)_2$, $\phi\text{-O}—CH_2CH_2(N^+(CH_3)_2)CH_2CH_2N(CH_3)_2Cl$, $\phi\text{-O}—CH_2CH(OH)CH_2N(NC_4H_4N)\phi2HCl$ or $\phi O—CH_2CH_2Cl$, or an analog thereof.

According to another aspect of the present invention, product compounds which can be obtained using a method according to the present invention are those compounds according to formula (IV):

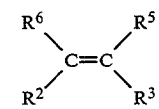

wherein $R^2$ is aryl or substituted aryl with substituents selected from alkyl, aryl, halo or alkoxyl; $R^3$ is hydrogen, alkyl, aryl or substituted aryl with substituents selected from alkyl, aryl, halo or alkoxyl; $R^5$ is hydrogen, alkyl, aryl or substituted aryl with substituents selected from alkyl, aryl or alkoxyl; and $R^6$ is one selected from the group consisting of (a) alkyl, aryl or aryl substituted in the position by alkyl, aryl, halo, alkoxyl, (b) acyl groups substituted with hydrogen, alkyl, ary, aryl or aryl optionally substituted by alkyl, aryl, halo, alkoxyl, (c) vinyl substituted with alkyl, aryl or substituted aryl substituted with alkyl, aryl, halo or alkoxyl or (d) alkynl groups —C≡C—$R^7$ where $R^7$ is hydrogen, alkyl, aryl or substituted aryl substituted with alkyl, aryl or alkoxyl.

According to the present invention, starting or intermediate compounds, which can be used in a method for producing or using haloenones or haloalkenes, can be compounds are those of formulae (IA), (IB), (IIA), (IIB), (IIIA) or (IIIB), as presented herein.

Product compounds which can be obtained using a method according to the present invention are those compounds are those of formulae (IB), (IC), (IIB), (IIC), (IID), (IIIB) or (IV) as presented above.

Non-limiting examples of enones used in methods according to the present invention include α-bromoenones; α-iodoenones; α-iodo, β-bromoenones; α-bromo,β-iodo enones; α-bromo, β-bromoenones; α-iodo, β-iodoenones; β-β-di-iodoenones; β-β-dibromoenones; α-bromo, β-β-dibromenones; and α-iodo, β-β-dibromoenones. Thus, the present invention provides an organic synthetic approach to biological compound derivatives and analogs, which synthetic methods provide commercially useful amounts of substituted enones and. alkeones in high yield and high specificity. Additionally, the use of different halogens at the β positions, such as iodine and bromine, allow for sequential, stereospecific and location specific substitution of haloenones and haloalkenes. Once the halogens of the haloenones are replaced by substituted or unsubstituted aryl or alkyl groups, conversion of the ketone to a methylene or any other functional group, which is readily derived from a ketone, can be accomplished by known method steps, and the present invention includes all of such additional known method steps As a non-limiting example, the methodologies of halogen replacement and ketone conversion are well known in the art, commonly called Stille ,chemistry. See, e.g. Stille, *Angew. Chem. Int. Ed. Engl.* 25:508 (1986), the entire contents of which reference is herein incorporated by reference Moreover, synthesis of the haloenones provides for the unexpectedly high stereospecificity, which synthesis method is now discovered to also provide high yields and selectivity, and the present invention includes all of such stereospecific methods utilizing haloenones and products obtained therefrom using known method steps. Stereospecificity of compounds obtained using methods of the present invention were greater than 80%, such 85, 90, 92, 93, 94, 95 and 97%. Conversion rates of compounds synthesized according to the present invention were greater than 50%, such as, 55, 60, 70, 75, 80, 83, 85, 87, 88, 89, 90, 91, 92, 93, 94 and 96%.

As a non-limiting example, the preparation of haloalkynols as starting materials for the synthesis of haloenones can be accomplished using halosuccinimides and silver ion catalysis in acetone, or with use of NXS/HTIB, wherein X is a halogen, such as I or Br.

Having now generally described the invention, the same will be further understood by reference to certain specific examples which are included herein for purposes of illustration only and are not intended to be limiting unless otherwise specified.

EXAMPLE 1

Synthesis of Substituted haloenones 4-bromo-2-phenyl-3-butyn-2-ol was synthesized from 2-phenyl-3-butyl-2-ol according to known methods using NBS in the presence of catalytic amounts of silver salts in acetone. See, e.g., Hofmeister et al *Angew. Chem. Int. Ed. Engl.* 23:727 (1984), the entire contents of which is herein incorporated by reference. The resulting 4-bromo-2-phenyl-3-butyl-2-ol (1 mmol) was treated with NIS (1 mmol) and HTIB (0.1 mmol) in acetonitrile (10 mL), for 18 hours at room temperature.

(Z)-4-bromo-4-iodo-3-phenyl-3-buten-2-one was formed in greater than 95% selectivity on a 72% conversion. Use of p-toluenesulfonic acid in place of HTIB gave a higher conversion of 93%, with 94% selectivity, of this compound A 95% conversion of 4-bromo-2-phenyl-3-butyl-2-ol to (Z)-4-bromo-4-iodo-3-phenyl-3-buten-2-one with 89% selectivity was obtained by the use of half molar quantities of iodine and HTIB in acetonitrile at room temperature. The product was a low melting solid (53°–55° C.) that was more often than not an oil, having NMR characteristics as follows: $^1$H NMR (CDCl$_3$) δ2.30 (s, 3H), 7.2–7.4 (m, 5H); 13C NMR (CDlC$_3$) δ28.6, 53.0, 127.9, 128.9, 129.0, 136.0, 200.5; IR (CHCl$_3$) 1690, 1580, 1380, 1240, 1170 cm$^1$; chemical analysis CH; mass spectrum M/z (relative intensity) 350/352 (M+, 14), 228 (C$_6$H$_5$C$_2$I, 72), 180/182 (C$_6$H$_5$C$_2$Br, 29), 101 (C$_6$H$_5$C$_2$, 19), 43 (CH$_3$CO, 100). In the next step the thus formed (Z)-4-bromo-4-iodo-3-phenyl-3-buten-2-one was converted to (E)-4-bromo-3,4-diphenyl-3-buten-2-one, by means of trimethylphenylstannane (equimolar) and Pd(P(C$_6$H$_5$)$_3$)$_2$Cl$_2$ (2 mol %) in THF at room temperature for 6 hours in 80% yield. (E)-4-bromo-3,4-diphenyl-3-buten-2-one had the following NMR: $^1$H-NMR δ2.28 (s, 3H), 7.35–7.4 (m, 5H) and 7.42–7.64 (m, 5H). This pattern was in contrast to that of the known (Z)-4-iodo-3,4-diphenyl-3-buten-2-one, which aromatic protons are situated at 7.0 (s, 5H), 7.1–7.25 (m, 3H) and 7.50–7.75 (m, 2H). See Janas et al *Tetrahedron Lett.* 26:1967 (1985), which is entirely incorporated by reference.

Accordingly, a β-,β-dihaloenone was synthesized and used as a starting material for the production of an aryl or alkylsubstituted enone, having high stereospecificity, high selectivity, and high yield, including tamoxifen.

EXAMPLE 2

Synthesis of substituted haloenone 4-bromo-2-phenyl-3-butyn-2-ol (0.230 g, 1.02 mmol), iodine pentoxide (0.304 g, 1.01 mmol) and iodine (0.260 g, 1.02 mmol) were added to methanol (75 ml) and the mixture was set to refluxing for 3 hours. The cooled mixture was poured into water (150 mL) and extracted with ether. The ether was washed with 5% thiosulfate solution and water. After drying over anhydrous, MgSO$_4$, the ether was evaporated. The residual yellow oil was triturated with methanol to give colorless crystals of (Z)-4-bromo-4-iodo-3-phenyl-3-butene-2-one; (mp 53°–55° C.); IR(CHCl$_3$) 3000, 1690, 1580, 1350, 1240, 1170 cm$^{-1}$; $^1$H NMR (CD Cl$_3$) δ2.30 (s, 3H) , 7.35–7.42 (m, 5H); $^{13}$C NMR (CDCl$_3$) δ28.6, 53.0, 127.9, 128.9, 129.0, 136.0, 200.5; yield, 80%.

EXAMPLE 3

Synthesis of substituted haloenone 4-bromo-2-phenyl-3-butyn-2-ol (1 mmol) was mixed with N-iodosuccinimide (1 mmol) and (hydroxy (tosyloxyl)iodo)benzene (HTIB) (0.1 mmol) in acetonitrile (10 mL) for 18 hours at room temperature. The mixture was added to water (50 mL) and extracted with ether. The work-up was as in Example 1. The conversion was 72%; the selectivity to the (Z)-4-bromo-4-iodo-3-phenyl-3-buten-2-one was 95%. In addition to the spectral results of Example 1, the following mass spectral data were obtained: M/z (relative intensity), 350/352 (M+, 14), 228 (C$_6$H$_5$C$_2$I, 72) 180/182 (C$_6$H$_5$Br, 29), 101 (C$_6$H$_5$C$_2$, 191), 43 (CH$_3$CO, 100).

EXAMPLE 4

Synthesis of substituted haloenones using p-toluene sulfonic acid for HTIB.

The quantities and procedures of Example 2 were repeated except that the catalyst HTIB was replaced with p-toluene sulfonic acid. The conversion was 93%. The selectivity to the (Z)-ketone was 94%.

EXAMPLE 5

Stereospecific synthesis of haloenone

4-Bromo-2-phenyl-3-butyn-2-ol (1 mmol) was mixed with iodine (0.5 m mol) and HTIB (0.5 m mol) in acetonitrile (10 mL) for 21 hours at room temperature. After the work-up procedures of Example 2, the yield of the (Z)-ketone was 85%.

EXAMPLE 6

Stereospecific synthesis of haloenone using ethyl acetate as solvent

The quantities and procedures of Example 2 were repeated except for the solvent which was ethyl acetate. Refluxing was used for 3 hours. The yield of the (Z)-ketone was 50%.

EXAMPLE 7

Stereospecific synthesis of haloenone

Under a nitrogen atmosphere, a Schlenk tube with a magnetic bar was charged with Pd(P $\phi_3$)$_2$ Cl$_2$ (0.01 mmol), freshly distilled tetrahydrofuran (2 mL), (Z)-4-bromo-4-iodo-3-phenyl-3-buten-2-one (0.5 mmol), trimethylphenylstannane (0.55K mmol) in that order. The mixture was stirred for 6 hours at room temperature. The solvent was evaporated and the crude product was chromatographed on alumina with hexane/ethyl acetate (9/1, v/v). The solvent was removed. The residual oil was dissolved in ether (10 mL) and washed with water. After drying and removing the ether, the residue (0.13 g, 80% yield) was (E)-4-Bromo-3,4-Diphenyl-3-buten-2-one: $^1$H-NMR (CDCl$_3$) $\delta$2.28 (s, 3H), 7.35–7.4 (m, 5H), 7.42–7.64 (M, 5H); Ms; M/z (Rel. Int.) 302/300 (70), 221 (70), 158/156 (36) 120(15), 43 (100)

EXAMPLE 8

Stereospecific synthesis of haloenone

A mixture of 1-(bromoethynyl)-cyclopentanol (212.5 mg, 1.12 mmol), iodine (1.22 mmol) and Koser's reagent (1.33 mmol) in acetonitrile (10 mL) was kept at room temperature away from light for 20 hours. The work-up was as in Example 1. VPC analysis indicated no starting material. The main product (80%) was an oil, (Z)-2-(bromoiodomethylidene) cyclohexanone; 1R (neat) 1700 (s), 1570 (m), 1530 (m), 1450 (m), 1300 (w), 1260 (s), 1240 (s), 1150 (s), 1140 (s), 1050 (m), 820 (m), 780 (s) cm$^{-1}$; MS, m/1 (Rel. intens.) 314/316 (M−,3), 286/288 (3), 131/133 (4), 127 (12), 79 (100); H-NMR (CDCl3) $\delta$1.81 (q, 2), 1.91 (q, 2), 2.48 (t, 2), 2.73 (t, 2); $^{13}$C-NMR (CDCl$_3$) $\delta$24.50, 25.32, 36.39, 42.05, 54.28, 147.14, 201.55.

EXAMPLE 9

Stereospecific synthesis of haloenone

A mixture of 1-(bromoethynyl)-2,2-dimethylcyclopentanol (244.5 mg, 1.13 mmol), iodine (1.21 mmol), and Koser's reagent (1.24 mmol) in acetonitrile (10 mL), was kept at room temperature away from light for 20 hours. After the work-up procedures of Example 1, an oil was isolated in 85% crude yield. It was purified by silica gel chromatography (with CH$_2$Cl$_2$/CCl$_4$ (1/1) as eluant and characterized as (Z)-2-(bromoiodomethylidene)-3,3-dimethylcyclohexanone; 214 mg (55% purified); 1R (neat) 1720 (s), 1570 (m), 1460 (s), 1370 (m), 1260 (m), 1180 (m), 1150 (m), 1100 (m), 1000 (s), 780 (s) cm$^{-1}$; MS, m/e (Rel. intens.) 342/344 (M+, 131, 187/189 (18), 136 (14), 107 (62), 93 (46), 69 (58), 51 (30), 41 (100); $^1$H-NMR (CDCl$_3$) $\delta$1.16 (s, 6), 1.74 (m, 4), 2.70 (m, 2); $^{13}$C-NMR (CDCl$_3$) $\delta$20.97, 23.85, 37.47, 40.68, 46.67, 51.72, 149.50, 206.85.

EXAMPLE 10

Stereospecific synthesis of haloenone

A mixture of 3-bromo-1-phenylpropynol (212 mg, 1.00 mmol), iodine (273 mg, 1.07 mmol) and Koser's reagent (441 mg, 1.12 mmol) in acetonitrile (10 mL) was kept at room temperature away from the light for 20 hours. Work-up was as in Example 1. No starting material was detected. The major product was mixed with iodobenzene and purifed by silical gel chromatography as in Example 8. The purified (60%) product was identified as (Z)-3-bromo-3-iodo-2-phenylpropenal: 1R (neat) 2880 (m) 2200 (m), 1690 (s), 1650 (m), 1500 (m), 1450 (m), 1270 (s), 1070 (s), 720 (s) cm$^{-1}$; MS, m/e (Rel. intens.) 336/338 (M+, 5), 257 (2), 209/211 (3), 181/183 (13), 102 (100) 75, (49), 51 (45); $^1$H-NMR (CDCl$_3$) $\delta$7.16 (m, 2), 7.44 (m, 3 ), 9.86 (s, 1 ).

EXAMPLE 11

Synthesis of haloenone

A mixture of 1-phenylethylnyl cyclopentanol (186 mg,, 1.0 mmol), NIS (225 mg, 1.0 mmol) and Koser's reagent (44.1 mg, 0.1 mmol) in methanol (10 mL) was kept at room temperature away from the light for 16 hours. Work-up was as in Example 1. No starting material was detected by gas chromatography. The product (80% yield) was 2-cyclopentylidene-2-iodo-1-phenylethanone. The data that support this assignment are as follows: IR 1660 (C=O) cm-1; GC/MS,m/z(rel.intens.) 312 (M,31), 185 (54), 105 (35), 77 (100); H-NMR (CDCl 3) § (8,9) 1.78 (m,4H), 2.25 (t, 6.6 H$_2$, 2H), 2.54 (t,v 6.9 H$_2$, 2H), 7.47 (t, 6H$_2$, 2H), 7.62 (d, 6H$_2$, 1H), 7.91 (d, 6H$_2$, 2H); C NMR (CDCl$_3$) $\delta$25.2, 28.5, 34.0, 40.8, 85.6, 128.5, 128.6, 129.7, 133.3, 134.5, 158.8, 192.8

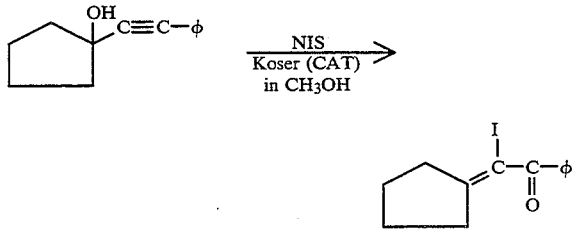

Example 12

Synthesis of haloenone

A mixture of 1-(1-butynyl) cyclopentanol (138 mg, 1 mmol), NIS (225 mg, 1 mmol) and Koser's reagent (44.1 mg, 0.1 mmol) in methanol (10 mL) was kept at room temperature away from the light for 14 hours. Work-up was as in Example 1; the major product was 1-cyclopentylidene-1-iodo-2-butanone formed in about 60% selectivity on a 100% conversion of starting material. The product was indentified by means of the following data: GC/MS, m/z (rel. intens.)264 (M, 6), 235 (14), 127 (7), 108 (8), 79 (100), 57 (36); H NMR (CDCl₃) § (8,9) 1.07 (t, 7.2 Hz, 3H), 1; 72(q, 6.9 Hz, 2 H), 2.48 (t, 6.9 Hz, 2H),, 2.72 (t, 6.9 Hz, 2 H), 2.89 (q, 7.2 Hz, 2H); ¹³C NMR (CDCl₃) 10.3, 26.1, 30.0, 36.9, 27.5, 45.8, 87.3, 168.0, 201.

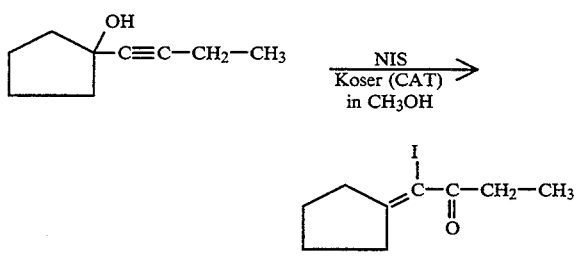

Example 13

Certain α-bromoethynyl cyclopentanols (1) undergo ring expansion when reacted with iodine and [(hydroxy-p-tosyloxyiodo]benzene (HTIB, Koser's reagent). (Janas, J. J.; Asirvatham, E. T.; McNelis, E. Tetrahedron Lett. 1985, 26, 1967. The products formed in acetonitrile were mixed (bromoiodomethylidene) cyclohexanones (2) with a predominance of Z-isomers.

These results were outgrowth of shifts of phenyl groups in linear d-tertiary alkynols to mixed β, β-dihaloenones. (Angara, G. J.; McNelis, E. Tetrahedron Lett. 1991, 32, 2099.

If X were bromine and Y+ an iodonium species generated by I₂/HTIB, the product was almost exclusively the Z-isomer. If X were iodine and Y+ a bromonium species formed by Br₂/HTIB, the product was a mixture of isomers with the Z-isomer the major isomer. A similar phenyl shift was noted for the α-secondary alkynol system 5 with the same preference for the Z-isomers. (Angara, G. J.; Bovonsombat, P.; McNelis,E. Tetrahedron Lett. 1992, 33, 7705.

In all of these series an unsymmetrical bridged halonium intermediate might be involved. Such vinyl cations should favor a site of greater charge stabilization. (Bovonsombat, P.; McNelis, E. Tetrahedron Lett. 1992, 33, 7705.) For halogen-containing alkynes, it should be the carbon not bearing the halogen (7). For aryl-containing alkynes, it should be the carbon bearing the aryl (8):

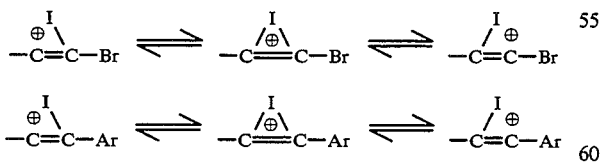

Indeed the first series of shifts in these reactions of α-alkynols with iodonium-producing reagents, such as iodine and iodine pentoxide in methanol, involved phenyl alkynes. (Stille, J. K.; Angew. Chem. Int. Ed. Engl. 1986, 255, 508. The tertiary alkynol 9 led to a mixture of iodoenones with the β-iodoenones 10 as the major product (60–80%).

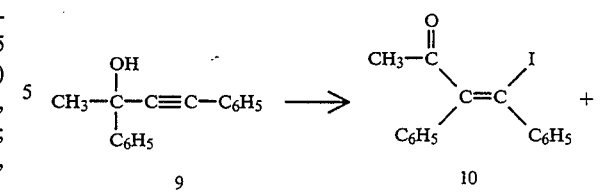

The minor product 11, an α-iodoenone, was isolated in 10–20% yields only after multiple column chromatographies. Related α-iodoenones, however, were the principal products when secondary alkynols were the substrates. (Moriiarty, R. M.; Vaid, R. K.; Koser,G. F. Synlett 1990, 365.

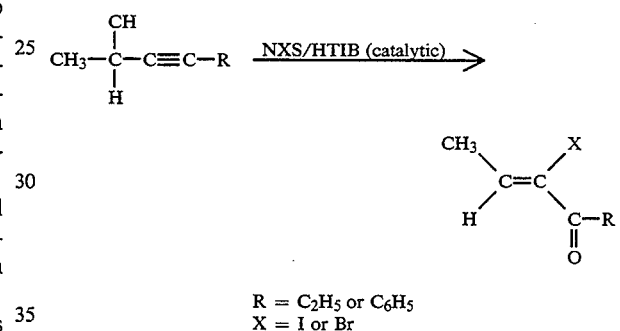

R = C₂H₅ or C₆H₅
X = I or Br

Until further information about these interesting rearrangements of secondary alkynols to α-haloenones is forthcoming, we refer to these changes as "Iodo-Meyer-Schuster" reactions (IMS) in analogy to the rearrangement of α-alkynols to enones in strong acid. (Bovonsombat, P.; McNelis, E. Tetrahedron 1993, 49, 1525). An examination of aryl groups in the cyclopentyl rearrangement is in order to establish the overall direction. In this report data will be presented to show that the IMS is the chief reaction. No evidence has been found to support a ring expansion analogous to that of the bromoalkynyl cyclopentanols 1.

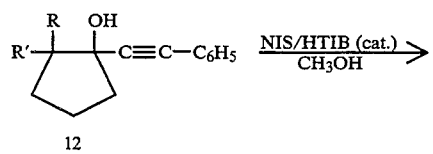

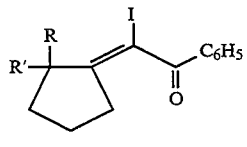

| | R | R' |
|---|---|---|
| a | H | H |
| b | CH₃ | CH₃ |
| c | CH₃ | H |

When compound 12a was treated with an equimolar amount of 1-iodo-2, 5-pyrrolidinedione (N-iodosuccinimide, NIS) and a tenth molar quantity of HTIB in methanol at room temperature overnight, compound 13a was formed in 80% yield. The spectral data that support the assignment of 2-(cyclopentylidene)-2-iodo-1-phenylethanone are as follows: IR (neat) 1660 (C=O)cm$^{-1}$; GC/MS, m/z (rel. int.) 312 (31,M+), 185 (54, M+-I), 105 (35,C$_6$H$_5$CO+), 77 (100, C$_6$H$_5$+); $^1$H-NMR (CDCl$_3$) δ1.78 (m, 4H), 2,25 (t, 6.6 Hz, 2H), 2.54 (t, 6.9 Hz, 2H), 7.47 (t, 6 Hz, 2H), 7.62 (d, 6 Hz, 1H), 7.91 (d, 6 Hz, 2H); $^{13}$C-NMR (CDCl$_3$) δ25.2 (c-3'), 28.5 (C-4'), 34.0 (syn to I, C-2'), 40.8 (C-5'), 85.6 (C-2), 128.5, 128.6, 129.7, 133.2, 133.3, 134.6, 158.8 (C-1'), 192.8 (C-1). These spectroscopic data can not be assigned to a cyclohexanone, a possible product if there were a ring expansion. Such a structure (14) would be the analogue of the bromoalkynol expanded product 2.

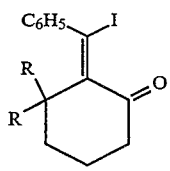

14

Most striking is the major appearance of a benzoyl fragment (105) in the mass spectrum in keeping with the IMS product 13 and not consonant with the ring expanded 14. The $^1$H-NMR lacks downfield signals around 2.7 ppm ascribable to the methylene protons α to the carbonyl of a cyclohexanone such as 14. There is a similar lack of absorbance in the $^{13}$C-NMR for such carbons between 42 and 46 ppm.

To put the structural assignment on a firmer footing, product 13a was treated with the deiodinating combination of Pd(CH$_3$CN)$_2$Cl$_2$ and Bu$_3$SnH to afford 2-cyclopentylidene-1-phenylethanone (15). This substance was identical to material prepared from the mercuric acetate/sulfuric acid hydration of alkynyl cyclopentanol 12a.

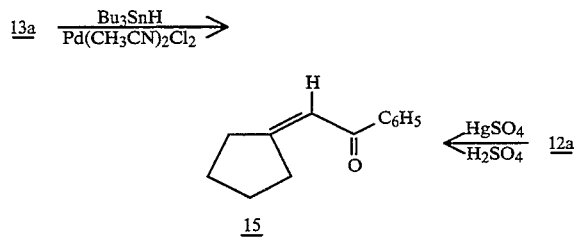

The spectral data that are in keeping with structer 15 area as follows: GC/MS m/z (rel. int.) 186 (13, M+), 158 (4, M-CO)+), 105 (44, C$_6$H$_5$CO+), 77 (100, C$_6$H$_5$+); $^{13}$C-NMR (CDCl$_3$) δ1.74 (m, 4H, 2.56 (t, 6.4 Hz, 2H), 2.92 (t, 6.4 Hz, 2.2 Hz subsplit, 2H), 7.00 (t, 2.2 Hz, 1H), 7.42 (m, 3H), 7.93 (m, 2H); IR (neat) 1675 cm$^{-1}$ (C=O).

In the ring expansions of the bromoalkynyl cyclopentanols there were marked preferences for (Z)-isomers. These effects grew out of the ability of iodine to form unsymmetrical bridges for the intermediate vinyl cations. (Janas, J. J.; Asirvatham, E. T.; McNelis,E. Tetrahedron Lett. 1985 26, 1967.) Such preferences were also present to a considerable degree in the formations of linear enones and enals. (Angara, G. J.; McNelis, E. Tetrahedron Lett. 1991., 32, 2099.)(Angara, G. J.; Bovonsombat, P.; McNelis, E. Tetrahedron Lett. 1992 33, 2285. A preference for Z-isomers was noted in the initial IMS studies with 2-hexynol (Moriarty, R. M.; Vaid, R. K.; Koser, G. F. Synlett 1990, 365). To examine this point in these phenylalkynyl cyclopentanol cases, a dimethyl analogue 12b and a monomethyl analogue 12c were investigated. The preferred stereoselectivities in these rearrangements are important since the product—be they α-iodoenones or β-iodoenones—can serve as templates for palladium-catalyzed exchange processes to a wide variety of alkyl or aryl enones of known stereochemistry.

When 2,2-dimethyl-1-phenylethynylcyclopentanol (12b) was treated with either NIS/HTIB (catalytic) in methanol or I$_{21}$/HTIB (1/1) in acetonitrile, a mixture of two compounds was formed in 70–90% yields. These compounds could not be separated by column chromatography. The carbonyl absorbance in the IR spectrum was at 1670 c$^{-1}$. The GC/MS results of each components differed slightly but both had major mass peaks as follows: 340 (M+), 283 ((M-C$_4$H$_9$)+), 213 ((M-I+), 157 (283-I), 127 (I), 105 (100%, C$_6$H$_5$CO+), 77 (96%, C$_6$H$_5$+). The values of 105 and 77 are in keeping with an IMS product and not one from a ring expansion. The $^1$H-NMR spectrum was analyzed as mixture of two sets of geometrical isomers of the IMS products 13b: (Z)-isomer, 1.05 (s,6H), 1.78 (m, 4H), 2.69 (t, 6.9 Hz, 2H), 7.44 (m, 2H), 7.53 (m, 1H), 8.00 (m, 2H); (E)-isomer, 1.42 (s, 6H), 1.55 (p. 6.9 Hz, 2H), 1.73 (t, 6.9 Hz, 2H), 2.39 (t, 6.9 Hz, 2H), 7,48 (m, 2H), 7.56 (m, 1H), 7.94 (m, 2H). The assignments of geometrical isomers hinged on the methyl absorbancies. The downfield methyl (1.42 ppm) was assigned to the (E)-isomer since its methyl groups would be syn to the carbonyl. Further, the (E)-isomer's protons at the C-6 position were upfield (2.39 ppm) from those of the (Z)-isomer (2.69 ppm), which were under the influence of the latter's carbonyl. The integrations of these absorbances led to a relative ratio of 1.5/1 for the Z/E isomers in acetonitrile. This ratio was reversed for the products of the reaction in methanol. Thus the yield of the Z-isomer would be 60% of the overall yield. With this value in hand, a 13C-NMR spectrum of the mixture was resolved as follows: (E)-isomer of 13b, (CDCl$_3$), 36.0 (C-4'), 43.4 (C-3'), 45.8 (C-5'), 46.6 (C-2'), 83.1 (C-2), 128.9, 129.2, 130.5, 130.8, 133.8, 133.9, 162.0 (C-1') , 194.8 (C-1).

Similar events took place with 2-methyl-1-phenylethynylcyclopentanol (13c). When 13c was treated with NIS/HTIB (catalytic) in methanol at room temperature for 18 hours, complete conversion took place. The reaction product with a carbonyl absorbance in the IR at 1670 cm$^{-1}$ was once more a mixture of two geometric isomers as indicated by NMR spectroscopies. The GC/MS determination demonstrated the formation of an IMS product 13c through the strong presence of the benzoyl fragments 105 (65%), 77 (100%). An M+ peak at 326 and an M+-I at 199 were also observed. The $^1$H-NMR analyses were as follows: (Z)-isomer of 13c, (CDCl$_3$)δ0.92 (d, 6.9 Hz, 3H), 2.2–2.5 (m, 5H), 2.94 (t, 6.9 Hz, 2H), 7.47 (t, 7.2 Hz, 2H), 7.58 (t, 7.2 Hz, 1H), 7.95 (t, 7.2 Hz, 2H); (E)-isomer of 13c, (CDCl$_3$)δ1.24 (d, 7.2 Hz, 3H), 2.2–2.5 (m, 6H), 2.84 (m, 1H), 7.47 (t, 7.2 Hz, 2H) 7.58 (t, 7.2 Hz, 1H), 7.95 (t, 7.2 Hz, 2H). The relative ratio of these isomers of 2-iodeo-2-(2'-methylcyclopentylidene)-1-phenylethyanone was about 2/1 (E/Z). Thus, for yield purposes, the E isomer of 13c represents approximately 67% of the total yields of 85% (crude) and of 65% (isolated). Extensions of assignments to a mixed $^{13}$C-NMR spectrume were as follows: (E)-isomer of 13c, δ19.6 (CH$_3$), 26.9 (C-4'), 34.1 (C-3'), 34.7 (C-5'), 45.9 (C-2'), 85.6 (C-2), 129.1, 130.1, 131.2, 131.3, 134.8, 135.6, 62.3 (C-1'), 194.2 (c-1); (Z)-isomer of 13c δ21.2 (CH$_3$), 24.1 (C-3'), 38.0 (C-4'), 40.7 (C-2'), 42.1 (C-5'), 87.4 (C-2), 129.1, 130.1, 131.2, 131.3, 134.8, 135.8, 163.2 (C-1), 194.0 (C-1) .

The sources of the lack of stereospecificity in the reactions of 12b and 12c have not been pinpointed and await further studies. Variations of solvent and acidic reagent were not helpful. For example, when the HTIB catalyst was replaced with p-toluenesulfonic acid (TsOH) in the NIS treatment of 12c in methanol, the IMS products were mixed with nearly equal quantities of the dehydrated starting material, 2-methyl-1-phenylethhynylcyclopentene (15b) and starting material.

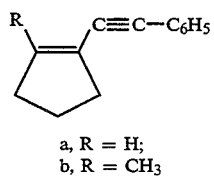

a, R = H;
b, R = CH$_3$

When acetonitrile was substitued for methanol in the NIS/HITIB (catalytic) system's reaction with 12c, the sole product was the cyclopentene 15b, whose GC/MS peaks were as follows: 182 (100%, M+), 167 (64), 152 (36), 115 (28). When compound 12a was treated with NIS/TsOH (catalytic)in acetonitrile, there was complete conversion to cyclopentene 15a. Major peaks in the GC/MS were 168 (100%, M+), 165 (45), 152 (48), 115 (18). If methanol were a replacement for acetonitrile, the reaction mixture contained almost equal quantities of 15a and the IMS product 13a. Thus simple variations of solvent or catalyst do not offer hope for resolving the E/Z ratios for 12b and 12c at present. The synthetic value of 13a is naturally not diminished.

Furthermore, the stabilization of the vinyl cation by the phenyl group is underscored by the milder reaction conditions such as NIS and catalytic amounts of HTIB versus iodine and stoichiometric amounts of HTIB. Similar stabilization of a vinyl cation by an ethyl group was achieved as well with NIS/HTIB (catalytic) as indicated below.

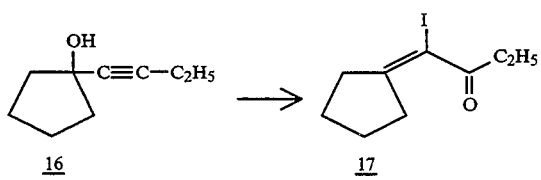

16          17

The directive effect of the phenyl on the unsymmetrically formed vinyl cations lead to an examination of a simple alkyl substituent. To that end 1-(1'-butynyl) cyclopentanol (16) was examined. That compound treated with an equimolar amount of NIS and a catalytic amount of HTIB in methanol. The major product was 1-cyclopentylidene-1-iodo-2-butanone (17) formed in about 60% selectivity on a 100% conversion of starting material. This main product was identified by means of the following data: MS: m/z (rel. int.) 264 (6,M+), 235 (14,M+-Et), 127 (7,I), 108 (8,M+-Et-I), 79 (100, C$_6$H$_7$+), 57 (36, CH$_3$CH$_2$CO+); $^1$H-NMR (CDCl$_3$) δ1.07 (t, 7.2 Hz, 3H, C-4), 1.72 (q, 6.9 Hz, 2H, C-4'), 1.89 (q, 6.9 Hz, 2H, C-3'), 2.48 (t, 6.9 Hz, 2H, 115 Hz subsplit, C-2' (Z-carbon)), 2.72 (t, 6.9 Hz, 2H, 1.5 Hz subsplit, C-5' (E-carbon)), 2.89 (q, 7.2 Hz, 2H, C-3); $^{13}$C-NMR (CDCl$_3$) δ10.3 (C-4), 26.1 (C-3'), 30.0 (C-4'), 36.9 (C-2'), 37.5 (C-5'), 45.8 (C-3), 87.3 (C-1), 168.0 (C-1'), 201.0 (C-2); IR (neat) 1675 cm$^{-1}$ A second product has not been isolated and characterized. The full conversion of the starting material was determined by the lack of its characteristic NMR's in any fraction which are as follows: $^1$H-NMR (CDCl$_3$) δ1.02 (t, 7.4 Hz, 3H), 1.78 (m, 8H), 2.09 (q, 7.4 Hz, 2H), 2.58 (s, 1H); $^{13}$C-NMR (CDCl$_3$) δ12.9 (C-4), 14.4 (C-3), 23.9 (C-3' & 4'), 43.0 (C-2' & 5'), 74.9 (C-1'), 84.0 (C-2), 85.0 (C-1).

If the product of 16 with NIS/HTIB (catalytic) were a ring expansion as were those with the corresponding bromoalkynyl cyclopentanols, the principal product would be 18.

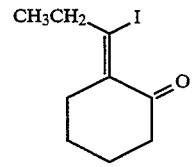

The protons on the carbon alpha to the six-membered ketone would be furthest downfield as they are in the bromoalkynol ring expansion −2.71 to 2.73 ppm. In such cases the protons are triplets. In this particular product the furthest downfiled signal is a quartet consistent with the methylene protons of the ethyl ketone. Furthermore, the observed chemical shift of that quartet is at 2.89 ppm. The related product of the IMS reaction of 2-hexynol, (Z)-4-iodo-4-hexen-3-one, exhibits the methylene quartet at 2.82 ppm. (Moriarty, R. M.; Vaid, R. K.; Koser, G. F. Synlett 1990, 365) Thus the IMS reaction of substituted ethynyl cyclopentanols prevail not only for a phenyl substitution but also for an alkyl substitution. If ring expanded products such as 14 and 18 are targeted, they may be obtained indirectly through the products of bromoethynyl cyclopentanols' reactions followed by an aryl or an alkyl exchange reactions catalyzed by palladium-containing species.

Experimental section $^1$H-NMR and $^{13}$C-NMR were recorded of CDCl$_3$ solutions containing tetramethylsilane as an internal standard on a GE-300 spectrometer and a Varian Gemini-200 spectrometer operated in the Fourier transform mode at 300 and 200 MHz in the proton mode and at 75.5 and 50 MHz in $^{13}$C mode, respectively. GC analyses were carried out on a Perkin-Elmer Sigma 3B gas chromatograph with a methyl silicone column (0.25 nn×50 m). GC/MS analyses were performed with a Hewlett-Packard 5992 with an OV-1 column (0.25 mm×15 m). IR spectra were obtained with a 137 Perkin-Elmer spectrophotometer and a Mattson Polaris FT-IR spectrophotometer. Products were purified by silica gel chromatography on J. T. Baker silica gel (40–140 mesh). Alkynols were purchased from Farchan Laboratories. Other reagents were obtained from the Aldrich Chemical Co. and solvents were received from the J. T. Baker Co. Elemental analyses were performed by Schwarzkopf Microanalytical Laboratory of Woodside, N.Y. High resolution mass analyses were performed with the Kratos Profile Mass Spectrometer.

Preparation of 2-methyl-1-phenylethynylcyclopentanol (12c)

2-Methylcyclopentanone (1.96 g, 19.9 mmol), dissolved in 10 mL of freshly distilled THF, was added dropwise via an additional funnel to an ice-bath cooled solution containing 25 mmol of lithium phenylacetylide (25 mL×1.0M) in 10 mL of THF. The reaction mixture during the addition was maintained at 0° C. and also kept under nitrogen purging. The reaction was maintained for an additional 2 hours at 0° C. and then stirred at room temperature for 18 hour. The THF solution was quenched by ice water mixture containing excess amounts of $NH_4Cl$. The aqueous solution was extracted by diethyl ether (2×75 mL). The ether layer was washed with water (3×50 mL) and dried with $MgSO_4$. According to GC analysis the conversion to the product was 80%. The product was isolated by means of silica gel column chromatography (40-140 mesh). The unreacted keetone was eluted as the first fraction with hexanes. The second fraction gave the product with diethyl ether as the eluant. After a complete solvent evaporation under vacuum, a solid was obtained in 60% yield (2.37 g). The product was characterized by spectroscopy: $^1$H-NMR (CDCl$_3$) δ61.14 (d, 3H), 1.43 (m, 1H), 1.80 (m, 2H), 2.13 (m, 4H), 7.31 (m, 3H), 7.44 (m, 2H); IR (nujol) 3300 (s), 1600 (m), 1450 (s), 1425 (m), 1400 (w), 1190 (m), 1070 (s), 1040 (s), 950 (m), 910 (m), 750 (s), 690 (s) cm$^{-1}$; MS m/z (rel. int.) Isomer A, 200 (M+, 12), 185 (M-CH$_3$, 23), 182 (16), 171 (100), 167 (14), 1676 (12), 165 (15), 157 (12), 155 (18), 153 (16), 152 (13), 143 (20), 142 (15), 141 (49), 139 (10), 129 (69), 128 (65), 127 (24), 115 (56), 91 (29), 101 (11), 77 (22); Isomer B, 200 (M+, 17), 157 (50), 144 (39), 143 (14), 130 (17), 129 (100), 117 (14), 115 (38), 102 (19), 91 (17), 77 (18); HR mass: Calcd; 200.1201. Found; 200.1603.

Preparation of 2,2-dimethyl-1-phenylethynylcyclopentanol (12b)

Lithium phenylacetylide (15 mL×1.0M, 15.0 mmol) was suspended in 10 mL of freshly distilled THF. A 10 mL THF solution of 2,2-dimethylcyclopentanone (1.28 g, 11.40 mmol) was added dropwise to the resulting suspension which was cooled at 0° C. and also purged under nitrogen. The reaction mixture was stirred at room temperature for 20 hours and quenched with a saturated solution of NH$_4$Cl. The aqueous solution was extracted with 2×75 mL of diethyl ether. The ether solution was washed with 3×50 mL of water and dried with MgSO$_4$. The product was isolated by means of silica gel column chromatography (40-140 mesh). Unreacted ketone and the by-product phenylethyne were washed off the column as the first fraction with CCl$_4$. The alkynol product was obtained as the second fraction with CH$_2$Cl$_2$/CCl$_4$ (1:1) solution as the eluant. After solvents evaporation under vacuum a solid was obtained in 41% yield (1.00 g). The alkynol was characterized by spectroscopy: $^1$H-NMR (CDCl$_3$) δ1.12 (s, 3H), 1.15 (s, 3H), 1.82 (m, 2H), 2.10 (m, 2H), 2.31 (m, 2H), 7.31 (m, 3H), 7.44 (m, 2H); IR (neat) 3480 (s), 1590 (w), 1490 (m), 1360 (m), 1260 (m), 1125 (m), 1070 (m), 970 (m), 900 (w), 860 (w), 750 (s), 690 (s) cm$^{-1}$; MS m/z (rel. int.) 214 (M+, 17), 199 (M-CH$_3$, 11), 171 (39), 157 (37), 145 (10), 144 (48), 143 (34), 131 (11), 130 (13), 129 (81), 128 (29), 127 (16), 117 (12), 116 (12), 115 (64), 103 (14), 102 (33), 1091 (11), 91 (27), 77 (36); HR mass: Calcd; 214.1358. Found; 214.1349.

Preparation of 2-cyclopentylidene-2-iodo-1-phenylethanone (13a)

1-Phenylethynyl-l-cyclopentanol (352 mg, 1.89 mmol) was dissolved in 20 mL of methanol. NIS (514 mg, 2.29 mmol) and HTIB (96 mg, 0.24 mmol) were added in one portion to the stirring solution. The reaction was protected from light and stirred at room temperature for 18 hours. The reaction mixture was diluted with 75 mL of diethyl ether and washed with 25 mL of 5% Na$_2$S$_2$O$_3$ solution and followed by 3×25 mL of water. The organic solution was dried with MgSO$_4$ and following filtration it was evaporated under vacuum to give a light green oil. The residue was subjected to a silica gel (40-40 mesh) column chromatography. Iodobenzene was eluted first with hexanes. The product was eluted next with 1:1 mixture Et$_2$O/ hexanes to yield a light green oil after solvent evaporation (329 mg, 56%). The product was characterized by spectroscopy: $^1$H-NMR (CDCl$_3$) δ1.75-1.84 (m, 4H), 2126 (t, 7 Hz, 2H), 2154 (t, 7 Hz, 2H), 7.47 (t, 6 Hz, 2H), 7.67 (d, 6 Hz, 1H), 7.91 (d, 6 Hz, 2H); $^{13}$C-NMR (CDCl$_3$) δ25.22, 28.53, 34.02, 40.85, 85.60, 128.57, 128.61, 129.70, 133.23, 133.30, 134.50, 158.84, 1.92.83; IR (CHCl$_3$) 1655 (s), 1590 (w), 1400 (w), 1300 (m), 1250 (s), 1220 (m), 1170 (m), 1050 (w), 1025 (w), 820 (w), 750 (s) cm$^{-1}$; MS m/z (rel. int.) 312 (M+, 2), 185 (M-I, 20), 184 (M-I-H, 11), 157 (13), 129 (11), 127 (I, 18), 115 (18), 105 (C$_6$H$_5$CO, 35), 80 (16), 77 (C$_6$H$_5$, 100; Anal. calcd for C13 H$_{13}$IO: C, 49.98; H, 4.21. Found: C, 50.54: H, 4.21.

Preparation of 1-cyclopentylidene-1-iodo-2-butanone (17)

1-Butynyl-1-cyclopentanol (146 mg, 1.06 mmol) was dissolved in 10 mL of methanol. NIS (256 mg, 1.14 mmol) and HTIB (45 mg, 0.12 mmol) were added in one portion to the stirring solution o The reaction mixture was protected from light and stirred at room temperature for 16 hours. The reaction wolution was worked up as usual. After solvent evaporation under vacuum a light green oil residue was obtained (264 mg). The residue was subjected to a silica gel (40-140 mesh) column chromatography. Iodobenzene was eluted first with hexanes. The product was obtained next with 1:1 mixture of CH$_2$Cl$_2$/hexanes and after solvent evaporation a light green oil was obtained (114 mg, 41%). The oil was characterized by spectroscopy: $^1$H-NMR (CDCl$_3$) δ1.07 (t, 3H), 1.70-1.94 (m, 4H), 2.48 (t, 7 Hz, 2H), 2.72 (t, 7 Hz, 2H), 2.89 (q, 7.3 Hz, 2H); $^{13}$C-NMR (CDCl$_3$) δ10.3, 26.13, 30.02, 36.86, 37.52, 45.83, 87.27, 168.02, 201.0; IR (neat) 1675 (s), 1570 (s), 1450 (m), 1400 (m), 1360 (m), 1320(m), 1270(s), 1130(s), 1050 (m), 880 (w), 860 (m), 770 (m) cm$^{-1}$; MS m/z (rel. int.) 264 (M+, 6), 235 (M-CH$_3$CH$_2$, 14), 127 (I, 7), 95 (13), 81 (23), 79 (100), 67 (19), 57 (CH$_3$CH$_2$CO, 36), 51 (46), 42 (17).

Preparation of 2-iodo-2-(2'-methylcyclopentylidene)-1-phenylethanone (13c)

NIS (220 mg, 0.98 mmol) and HTIB (39 mg, 0.98 mmol) were added in one portion to a stirring solution containing 2-methyl-1-cyclopentanol in 10 mL of methanol. The reaction mixture was protected from light and stirred at room temperature for 16 hours. The reaction was worked up as usual. After evaporation of solvent under vacuum a light green oily residue was obtained (323 mg). The GC/Ms spectrum of the crude residue showed that starting material was present along with iodobenzene and the product. The product was isolated by means of silica gel column chromatography (40-140 mesh). Iodobenzene was eluted first with hexanes. The product was eluted next with 1:1 mixture of CH₂Cl₁₂/hexanes and after solvent evaporation under vacuum, a light green oil was obtained (86.2 mg, 28%). The oil was characterized by spectroscopy: ¹H-NMR (CDCl₃): (E-isomer) δ1.24 (d, 7.2 Hz, 3H), 2.20–2.96 (m, 7H), 7.47 (t, 7.2 Hz, 2H), 7.58 (t, 7.2 Hz, 1H), 7.92 (d, 7.8 Hz, 2H); (Z-isomer); δ0.92 (d, 7.2 Hz, 3H), 2.20–2.96 (m, 7H), 7.47 (t, 7.2 Hz, 2H), 7.58 (t, 1H), 7.96 (d, 8 Hz, 2H); ¹³C-NMR (CDCl₃) (Z-isomer) δ21.23, 24.07, 38.0, 40.69, 42.06, 87.39, 129.91, 130.1, 131.2, 131.32, 134.79, 135.76, 163.22, 194.02; (E-isomer) δ19.62, 26.87, 34.09, 34.72, 45.95, 85.55, 130.05, 131.19, 134.79, 135.59, 162.29, 1.94.20; IR (neat) 1665 (s), 1590 (w), 1450 (m), 1350 (w), 1300 (m), 1245 (s), 1175 (m), 1050 (m), 1015 (m), 975 (w), 690 (m) cm⁻¹; MS m/z (rel. int.) 326 (M+, 5), 311 (M-Ch₃, 5), 199 (M-I, 11), 157 (49), 129 (25), 105 (C₆H₅CO, 55), 77 (C₆H₅, 100).

Preparation of 2-(2', 2'-dimethylcyclopentylidene) -2-iodo-1-phenylethanone (13b)

2,2-Dimethyl-1-phenylethynyl-1-cyclopentanol (145 mg, 0.68 mmol) was dissolved in 10 mL of methanol. NIS (198 mg, 0.85 mmol) and HTIB (36 mg, 0.09 mmol) were added in one portion to the stirring solution at room temperature. The reaction was protected from light and stirred at room temperature for 18 hours. The reaction misture was worked up as usual. After complete evaporation of solvents under vacuum, a light green residue was obtained. The product was isolated by means of silica gel preparative TLC (1:1, CH₂Cl₂/hexanes, Rf=0.45) to give a light green solid after solvents evaporation (44 mg, 19%). It was characterized by spectroscopy: ¹H-NMR (CDCl₃) (E-isomer) δ1.42 (s, 6H), 1.23–1.78 (m, 4H), 2.39 (t, 7 Hz, 2H), 7.47 (t, 2H), 7.56 (t, 7.5 Hz, 1H), 7.94 (d, 7.5 Hz, 2H); (Z-isomer) δ1.05 (s, 6H), 1.23–1.78 (m, 4H), 2.69 (t, 7 Hz, 2H), 7.47 (t, 2H), 7.58 (t, 7.2 Hz, 1H), 8.00 (d, 7.5 Hz, 2H); ¹³C-NMR (CDCl₃) (Z-isomer) δ22.15, 27.92, 35.99, 43.43, 46.58, 83.06, 128.87, 129.25, 130.46, 130.76, 133.82, 133.95, 162.05, 194.82; (E-isomer) δ23.78, 26.27, 30.28, 37.54, 45.70, 81.67, 128.87, 129.25, 130.46, 130.76, 133.82, 133.95, 158.78, 192.86; IR (CHCl₃) 1660(s), 1590(w), 1450(m), 1300 (w), 1230 (s), 1075 (s), 1045 (s), 875 (m), 750 (s) cm⁻¹; MS m/z (rel. int.) 340 (M+, 4), 297 (M-CH₃CH₂CH₂, 4), 283 (M-CH₃(CH₂)₃, 4), 213 (6), 157 (7), 143 (6), 131 (8), 127 (I, 8), 115 (11), 105 (C₆H₅CO, 46), 91 (42), 79 (26), 77 (C₆H₅, 100 ).

Preparation of 2-cyclopentylidene-1-phenylethanone (15)⁸

1-Phenylethynyl-1-cyclopentanol (229 mg, 1.22 mmol) was suspended in an acidic solution of HgSO₄ (10 mL of a solution of 574 mg of yellow HgO in 3 mL H₂So₄ and 15 mL H₂O solution) The suspension was heated at 60°–75° C. for 2 hours. The reaction was cooled and poured into 50 mL of ice/water and extracted with 50 mL of diethyl ether. The ether layer was washed several times with saturated solution of Na₂CO₃ until the aqueous layer was basic. The organic layer was further washed with 3×50 mL of water and dried with MgSO₄. After complete evaporation of solvents under vacuum, a reddish residue was obtained. The residue was then subjected to silica gel column chromatography (40–140 mesh). The product was obtained as the third fraction with 1:1 CH₂Cl₂/pet ether as the eluting solvent (Rf=0.60). The product after solvent evaporation was a light green oil (49 mg, 22%). It had the following spectra: ¹H-NMR (CDCl₃) δ1.61–1.84 (m, 4H) , 2.56 (t, 6.4 Hz, 2H), 2.92 (t, 6 Hz, 2H), 7.00 (t, 2 Hz, 1H) , 7.38–7.52 (m, 3H) , 7.94 (d, 6.5 Hz, 2H); ¹³C-NMR (CDCl₃) 625.97, 27.22, 34.39, 37.32, 116.31, 128.43, 128.85, 128.96, 132.44, 133.40, 139.88, 171.50, 190.76; IR (neat) 1660 (s), 1610 (s), 1440 (m), 1370 (m), 1230 (s), 1175 (m), 1045 (m), 1020 (m), 1000 (m), 850 (w), 830 (m), 730 (m), 720 (m), 700 (s) cm⁻¹; MS m/z (rel. int.) 186 (M+, 13), 157 (13), 128 (12), 105 (C₆H₅CO, 44), 77 (C₆H₅, 100).

Preparation of 2-cyclopentylidene-1-phenylethanone (15) via iodide exchange

Pd(CH₃CN)₂Cl₂ (126 mg, 0.50 mmol) was placed in a 5 mL round-bottomed flask and purged withN₂. 2-Cyclopentylidene-2-iodo-1-phenylethanone (13a) 136 mg, 0.44 mmol) dissolved in 2.5 mL of THF was added via syringe to the flask counting the Pd complex. The solution was purged with N₂ and stirred at room temperature. After 5 minutes at room temperature, Bu₃SnH (187 mL, 0.44 mmol) was added which resulted in an immediate precipitation of Pd°. The solution was filtered to remove the Pd metal. The solvents were removed under vacuum to afford a reddish residue. The product was isolated by means of silica gel column chromatography (40–140 mesh). The product, 2-cyclopentylidene- 1-phenylethanone (15), was obtained as the second fraction with 1:1 mixture of CH₂Cl₂/pet ether. The initial fraction contained tin by-products. The product was obtained with quantitative yields and was characterized by spectroscopy. Its spectra matched those of compound 15, obtained from mercuric hhydration of 1-phenylethynyl-1-cyclopentanol. (Venus-Danilova, E. D.; Gorelik, M. V. Zhur. Obshchei. Khim. 1953, 23, 1139; Chem. Abstr. 1953, 47, 12211b.)

Example 14

Ring Expansion of an α-Bromoalkynol Camphor by Means of Iodine and Koser's Reagent The reaction of α-alkynols with iodonium-producing reagents have come under scrutiny as of late, because they are novel modes of forming α-iodoenones, β-iodoenones and mixed β, β-bromoiodoenones. (Janas, J. J.; Asirvatham, E. T.; McNelis, E. Tetrahedron Lett. 1985, 26, 1967; Angara, G. J.; McNelis, E.Tetrahedron Lett. 1991, 32, 2099; Angara, G. J.; Bovonsombat, P.; MeNelis, E. Tetrahedron Lett. 1992, 33, 2285; Bovonsombat, P.; McNelis, E. Tetrahedron Lett. 1992, 33, 7705.) Since such compounds are formed stereospecifically frequently, they are simple templates for the construction of more complex molecules via selective metal-catalyzed coupling reactions (Stille, J. K.; Angew. Chem. Int. Ed. Engl. 1986, 25, 508.) Recent noteworthy examples of these reactions are the ring expansions of α-alkynylcyclopentanols with iodine and Koser's reagent (Moriarty, R. M.; Vaid, R. K.; Koser, G. F. Synlett 1990, 365.) (HTIB, [hydroxy(tosyloxy)iodo]benzene) . (Bovonsombat, P.; McNelis, E. Tetrahedron 1993, 49, 1525.)

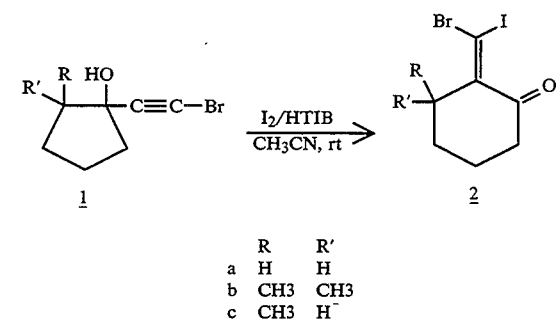

| | R | R' |
|---|---|---|
| a | H | H |
| b | CH3 | CH3 |
| c | CH3 | H |

The yields of these ring expansions ranged from 75 to 82%. The preponderances of Z-isomers vary from greater than 12/1 for 2a, through 7/1 for 2b and 3.3 for 2c. In this report we wish to present a significant extension of such expansions to a camphor-based system to obtain a product suitable for enantiospecific syntheses.

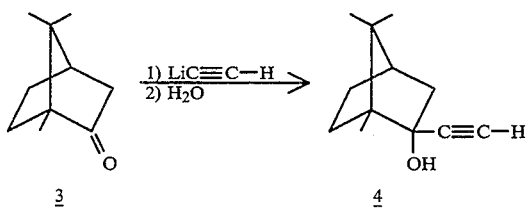

To this end, (1R)-(+)-camphor (3) was treated with lithium acetylide to afford 2-exo-ethynyl-1,7,7-trimethylbicyclo[2.2.1]heptan-2-ol (4). This low melting solid (mp. 57.5°–59.5° C.; lit. 61°–62° C.) had the same IR, $^1$H-NMR and $^{13}$C-NMR as reported by Lane and colleagues. (Johnson, C. D.; Lane, S.; Edwards, P. N.; Taylor, P. J. J. Org. Chem. 1988, 53, 5130.) Compound 4 was treated with 1-bromo-2, 5-pyrrolidinedione (NBS) and a catalytic amount of silver nitrate in acetone to form the bromoalkynol 5, 2-exobromoethynyl-1,7,7-trimethylbicyclo [2.2.1]heptan-2-ol in 90% yield. (Hofmeister, h.; Annen, K.; Laurent, H.; Welcherr, R. Angew. Chem. Int. Ed. Eng. 1984, 23,727.) This solid (mp 60.5°–62.5° C.) had the following spectral properties: IR (nujol) 3480 (s), 2200 (w), 1060 (s), 1000 (m), 975 (m), 760 (m), 740 (m) cm$^{-1}$; $^{13}$C-NMR (CDCl$_3$) δ10.8, 21.5, 21.9, 27.4, 30.3, 33.0, 43.7, 45.9, 48.5, 54.4, 79.7, 84.7; GC/MS m/z (rel. int.) 177 (6, M+-Br), 133 (18), 110 (40), 95 (100), 41 (33). Since the three absorbances in the $^{13}$C-NMR spectrum of 5 assignable to the methyl carbons were the same to those of 4 (10.8, 21.5 and 21.9), there would appear to have been no isomerization of the exoalkynyl group to its endo-isomer.

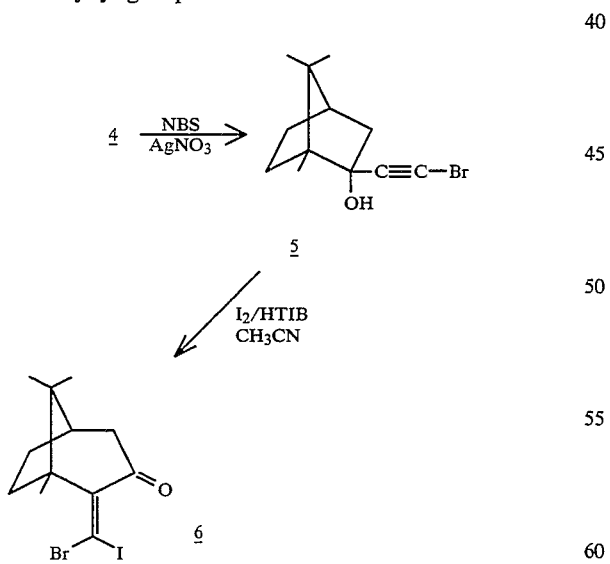

The bromoalkynol 5 was then reacted with equimolar amounts of iodine and [hydroxy(tosyloxy)iodo]benzene (Koser's reagent, HTIB) in acetonitrile at room temperature overnight. The ring-expanded product 6 (mp 50.5°–51.5° C.) was formed in 60% yield (isolated; 85% byGC). The following spectral and analytical data are consistent with the structural assignment of 6 as 2-[(Z) -bromoiodomethylidene]-1,8,8-trimethylbicyclo[3.2.1]octan-3-one: IR (nujol) 1700 (s), 1560 (m), 1220 (m), 1200 (m), 960 (m), 770 (s) cm−; $^1$H-NMR (CDCl$_3$) δ0.88 (s, 3H), 0.96 (s, 3H), 1.04 (s, 3H), 1.52 (m, ? .H), 1.77 (m, 2H), 2.01 (m, 1H), 2.14 (m, 1H), 2.57 (dt, 1H), 2.90 (dd, 1H); $^{13}$C-NMR (CDCl$_3$) 614,5 (anti CH$_3$-8), 20.2 (syn CH$_3$-8), 24.6 (CH$_3$-1), 28.6 (C-7), 33.6 (C-8), 41.3 (C-6), 46.2 (C-1), 47.3 (C-5), 58.3 (C-4), 58.9 (CBrI), 144.5 (C-2), 203.1 (C-3); GC/MS m/z (rel. int.) 382/384 (M+,4), 354/356 ((M-CO)+, 4), 227/229 ((M-CO—I)+, 10) 148 ((M-CO—I—Br)+, 24), 91 (34), 41 (100); anal. CH. The presence of a carbonyl in 6 is clear from the $^{13}$ C-NMR (203.1 ppm) and the IR spectra (1700 cm$^{-1}$). The mass spectral data has bearing on the alkene assignment. The pattern of M+ (382/384) followed by (M-CO)+ (354/356) and (M-CO—I)+(227/229) is one that resembles the cracking pattern of Z-isomers of substituted 2-bromoiodomethylidene cyclohexanones. (Bovonsombat, P.; McNelis, E.Tetrahedron 1993., 49, 1525. ) The cracking pattern for the related E-isomers is M+, then (M-I)+ followed by (M-I—CH$_2$CO)+. No such peaks are seen in the pattern of 6.

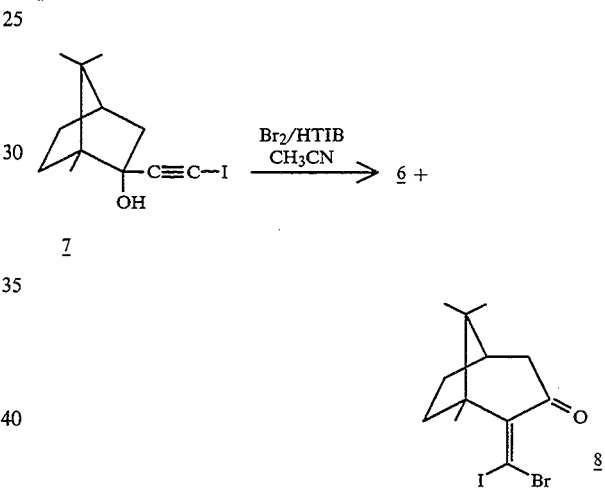

In contrast to the stereospecific ring expansions and shift induced by iodonium ions, similar reactions of iodoalkynols with bromine/HTIB have been shown to be devoid of any useful degree of sterospecificity of the bromonium ion. In the case of rearrangements of linear iodoalkynols with Br$_2$/HTIB, the principal product was not an E-isomer but the Z-isomer. Indeed, in the case of 3-iodo-1-phenylpropynol the Z-isomer was formed in 46% whereas the E-isomer's yield was 22%. (Bovonsombat, p.; McNelis, E. Tetrahedron Lett. 1992 33, 7705) For 4-iodo-2-phenyl-3-butyn-2-ol and with half molar amounts of Br$_2$/HTIB in acetonitrile, the yield of the (Z)-4-bromo-4-iodo-3-phenyl-3-buten-2-one was 59% and that of the E-isomer was 10%. (Angara, G. J.; Bovonsombat, P.; McNelis, E.Tetrahedron Lett. 1992 33, 2285.) In this work, similar behavior with bromine/HTIB inCH$_3$CN was observed with 2-exo-iodoethynyl-1,7,7-trimethylbicyclo[2.2.1]heptan-2-ol (7). Two major and several minor products were formed. Separations have been difficult and are incomple but GC/MS data exhibit 6 to be one of the major products in at least 40% yield. A cracking pattern ascribable to an E-isomer (loss of iodine prior to loss of CO) such as 8 is observed for the other major product.

As in the other cased the mixture obtained by the reactions of bromine and iodoalkynols contrast sharply with the high yelds and purity of the products of reactions between iodine/HTIB and bromoalkynols. Such Z-bromoiodoenones represent flexible entries to may substituted alkyl or aryl enones by means of selective coupling catalyzed by organometallic catalysts. Furthermore, if the coupling substituents are chiral, the products should be formed in high enantioselectivity in light of the proximate camphor-derived system. Mild cleavages such as with ozone would lend to a broad range of optically active ketones. The results of such ongoing direction is will be reported subsequently.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

I claim:

1. A method for the production of an alkene or enone, comprising the steps of:

reacting an alkyne or alkynol of the formula (IA) or (IB), respectively,:

$$R^{10}-C\equiv CH \quad (IA)$$

$$R^1-\underset{R^2}{\underset{|}{\overset{OH}{\underset{|}{C}}}}-C\equiv CH \quad (IB)$$

wherein $R^{10}$ is optionally substituted alkyl or aryl; $R^1$ is hydrogen or an optionally substituted alkyl or aryl group; and $R^2$ is an optionally substituted aryl group; or $R^1$ and $R^2$ combine to form a cyclic group of the formula

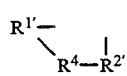

in which $R^{1'}$ is optionally substituted methylene and $R^{2'}$ is methylene and $R^4$ is alkyl, O, cycloalkyl, cycloaryl, heterocycloalkyl or heterocycloaryl, with N—$X^1$-succinimide, in which $X^1$ is bromine or iodine, in the presence of a catalytic amount of silver salt in an appropriate solvent under conditions satisfactory to produce a haloalkyne or haloalkynol of formula (IIA) or (IIB):

$$R^{10}-C\equiv C-X^1 \quad (IIA)$$

$$R^1-\underset{R^2}{\underset{|}{\overset{OH}{\underset{|}{C}}}}-C\equiv C-X^1 \quad (IIB)$$

and then producing a haloalkene or haloenone of formula (IIIA) or (IIIB):

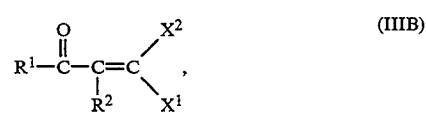

wherein $X^2$ is bromine or iodine, by reacting said haloalkyne or haloalkynol of formula (IIA) or (IIB) (a) with N—$X^2$-succinimide or $(X^2)_2$ in the presence of a catalytic amount of (hydroxy(tosyloxy)iodo)benzene or p-toluene sulfonic acid, or (b) with $I_2/I_2O_5$, in which case $X^2$ is iodine, under conditions satisfactory to produce a haloalkene or haloenone of formula (IIIA) or (IIIB).

2. A method in accordance with claim 1, wherein said alkyne or alkynol of the formula (IA) or (IB) is an alkyne of the formula (IA), said haloalkyne or haloalkynol of formula (IIA) or (IIB) is a haloalkyne of formula (IIA), and said haloalkene or haloenone of formula (IIIA) or (IIIB) is a haloalkene of formula (IIIA).

3. A method in accordance with claim 1, wherein said alkyne or alkynol of the formula (IA) or (IB) is an alkynol of the formula (IB), said haloalkyne or haloalkynol of formula (IIA) or (IIB) is a haloalkynol of formula (IIB), and said haloalkene or haloenone of formula (IIIA) or (IIIB) in a haloenone of formula (IIIB).

4. A method in accordance with claim 3, wherein $R^1$ and $R^2$ combine to form a cyclic group of the formula

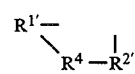

in which $R^{1'}$ and $R^{2'}$ are each methylene and $R^4$ is alkyl, O, cycloalkyl, cycloaryl, heterocycloalkyl or heterocycloaryl.

5. A method in accordance with claim 4, wherein $R^{1'}$, $R^4$ and $R^{2'}$ combine with the other two ring carbon atoms to form 1–4 cyclo or heterocyclo ring structures of 4, 5 or 6 members.

6. A method in accordance with claim 1, further including the steps of:

reacting the haloalkene or haloenone of formula (IIIA) or (IIIB) with an $R^5$—Sn/Pd or $R^5$—Zn/Pd complex under conditions satisfactory to produce a haloalkene or haloenone of the formula (IVA) or (IVB):

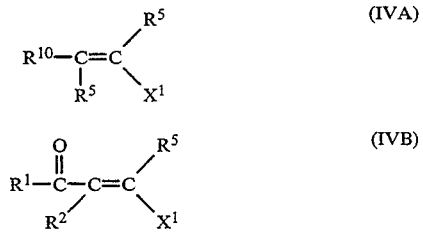

wherein $R^5$ is optionally substituted alkyl or aryl.

7. A method in accordance with claim 6, wherein said alkyne or alkynol of the formula (IA) or (IB) is an alkyne of the formula (IA), said haloalkyne or haloalkynol of formula (IIA) or (IIB) is a haloalkyne of formula (IIA), said haloalkene or haloenone of formula (IIIA) or (IIIB) is a haloalkene of formula (IIIA), and said haloalkene or haloenone of formula (IVA) of (IVB) is a haloalkene of formula (IVA).

8. A method in accordance with claim 6, wherein said alkyne or alkynol of the formula (IA) or (IB) is an alkynol of the formula (IB), said haloalkyne or haloalkynol of formula (IIA) or (IIB) is a haloalkynol of formula (IIB), said haloalkene or haloenone of formula (IIA) or (IIB) in a haloenone of formula (IIIB), and said haloalkene or haloenone of formula (IVA) or (IVB) is a haloenone of formula (IVB).

9. A method in accordance with claim 8, wherein $R^1$ and $R^2$ combine to form a cyclic group of the formula

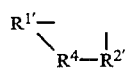

in which $R^{1'}$ and $R^{2'}$ are each methylene and $R^4$ is alkyl, O, cycloalkyl, cycloaryl, heterocycloalkyl or heterocycloaryl.

10. A method in accordance with claim 9, wherein $R^{1'}$, $R^4$ and $R^{2'}$ combine with the other two ring carbon atoms to form 1–4 cyclo or heterocyclo ring structures of 4, 5 or 6 members.

11. A method in accordance with claim 6, further including the step of reacting said haloalkene or haloenone of the formula (IVA) or (IVB) with an $R^3$—Sn/Pd or $R^3$—Zn/Pd complex under conditions satisfactory to produce an alkene or enone of the formula (VA) or (VB):

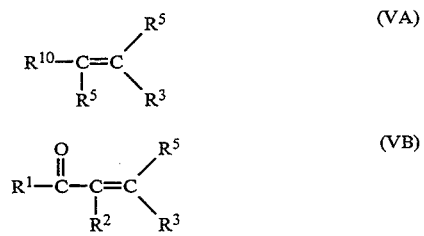

wherein $R^3$ is optionally substituted alkyl or aryl.

12. A method in accordance with claim 11, wherein said alkyne or alkynol of the formula (IA) or (IB) is an alkyne of the formula (IA), said haloalkyne or haloalkynol of formula (IIA) or (IIB) is a haloalkyne of formula (IIA), said haloalkene or haloenone of formula (IIIA) or (IIIB) is a haloalkene of formula (IIIA), said haloalkene or haloenone of formula (IVA) of (IVB) is a haloalkene of formula (IVA), and said alkene or enone of the formula (VA) or (VB) is an alkene of the formula (VA).

13. A method in accordance with claim 11, wherein said alkyne or alkynol of the formula (IA) or (IB) is an alkynol of the formula (IB), said haloalkyne or haloalkynol of formula (IIA) or (IIB) is a haloalkynol of formula (IIB), said haloalkene or haloenone of formula (IIIA) or (IIIB) in a haloenone of formula (IIIB), said haloalkene or haloenone of formula (IVA) or (IVB) is a haloenone of formula (IVB), and said alkene or enone of the formula (VA) or (VB) is an enone of the formula (VB).

14. A method in accordance with claim 13, wherein $R^1$ and $R^2$ combine to form a cyclic group of the formula

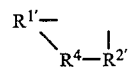

in which $R^{1'}$ and $R^{2'}$ are each methylene and $R^4$ is alkyl, O, cycloalkyl, cycloaryl, heterocycloalkyl or heterocycloaryl.

15. A method in accordance with claim 14, wherein $R^{1'}$, $R^4$ and $R^{2'}$ combine with the other two ring carbon atoms to form 1–4 cyclo or heterocyclo ring structures of 4, 5 or 6 members.

16. A method in accordance with claim 13, further including the step of converting said enone of formula (VB), by means of the Clemmensen or Wolff-Kishner reactions, to an alkene of the formula (VI):

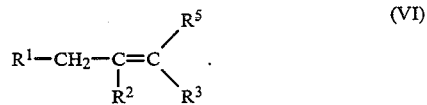

17. A method in accordance with claim 4, further including the steps of:
reacting the haloenone of formula (IIIB) with an $R^5$—Sn/Pd or $R^5$—Zn/Pd complex under conditions satisfactory to produce an enone of the formula (VII):

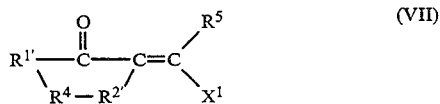

wherein $R^5$ is optionally substituted alkyl or aryl.

18. A method in accordance with claim 17, further including the step of reacting said enone of the formula (VII) with an $R^3$—Sn/Pd or $R^3$—Zn/Pd complex under conditions satisfactory to produce an enone of the formula (VIII):

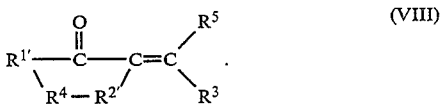

19. A method in accordance with claim 18, further including the step of converting said enone of formula (VIII), by means of the Clemmensen or Wolff-Kishner reactions, to an alkene of the formula (IX):

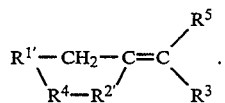

(IX)

20. A method in accordance with claim 12, wherein $R^5$ is $-\phi$; $R^3$ is $-CH_2CH_3$; and $R^{10}$ is selected from the group consisting of $-\phi-O-CH_2CH_2N(CH_3)_2$, $-\phi-O-CH_2CH_2(N^+(CH_3)_2)CH_2CH_2N(CH_3)_2Cl$, $-\phi-O-CH_2CH(OH)CH_2N(NC_4H_4N)\phi 2HCl$ and $-\phi-O-CH_2CH_2Cl$.

21. A method in accordance with claim 12, wherein $R^5$ is an aryl radical optionally substituted by one or more alkyl, alkoxy and/or dialkylamino-alkoxy radicals; $R^3$ is an alkyl radical; and $R^{10}$ is $-\phi-O-(CH_2)_nNR^8 R^9$ in which $R^8$ and $R^9$ are $C_{1-6}$ alkyl radicals or wherein the $-N-R^8R^9$ group is a nitrogen-containing heterocyclic radical.

* * * * *